Figure 1:
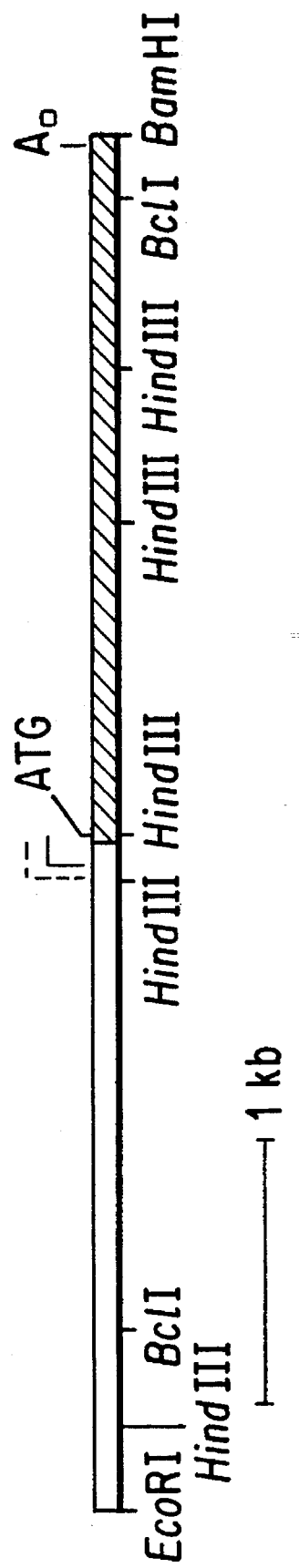

United States Patent [19]
Mintz

[11] Patent Number: 5,550,316
[45] Date of Patent: Aug. 27, 1996

[54] TRANSGENIC ANIMAL MODEL SYSTEM FOR HUMAN CUTANEOUS MELANOMA

[75] Inventor: Beatrice Mintz, Elkins Park, Pa.

[73] Assignee: Fox Chase Cancer Center, Philadelphia, Pa.

[21] Appl. No.: 11,060

[22] Filed: Jan. 29, 1993

Related U.S. Application Data

[63] Continuation-in-part of Ser. No. 636,798, Jan. 2, 1991, abandoned.

[51] Int. Cl.$^6$ .................... C12N 15/00; A01K 67/00
[52] U.S. Cl. .............. 800/2; 800/DIG. 1; 435/172.3; 536/23.1; 536/23.72; 536/24.1; 424/9.2
[58] Field of Search .................. 800/2, DIG. 1; 435/172.3; 536/23.1, 23.72, 24.1; 424/9

[56] References Cited

PUBLICATIONS

B Mintz et al (1993) Proc Natl. Acad. Sci USA 90:8817–8821.
R Halaban (1991) Cancer Metastasis Rev 10(2):129–140.
M Bradl et al (1991) Proc Natl Acad Sci, USA 88:164–168.
K N Broadley et al (1989) Laboratory Investigation 61:571–575.
Hesketh (1995) The Oncogene Facts Book, pp. 32–42.
Strojek et al (1988) Genetic Engineering: Principles and methods, 10:238.
Loudon et al (1993) Clin Exp Pharmacol Physiol 20: 283–288.

*Primary Examiner*—Jacqueline M. Stone
*Assistant Examiner*—Bruce R. Campell
*Attorney, Agent, or Firm*—Pennie & Edmonds

[57] ABSTRACT

The present invention relates to transgenic animal model systems for human cutaneous melanoma. It is based, at least in part, on the discovery that, in susceptible transgenic mice, accelerated formation of melanoma tumors occurred near the wound borders of skin grafts carrying the Tyr-SV40E transgene, indicating that factors present during wound healing facilitate the formation of cutaneous melanoma in susceptible tissue.

2 Claims, 13 Drawing Sheets

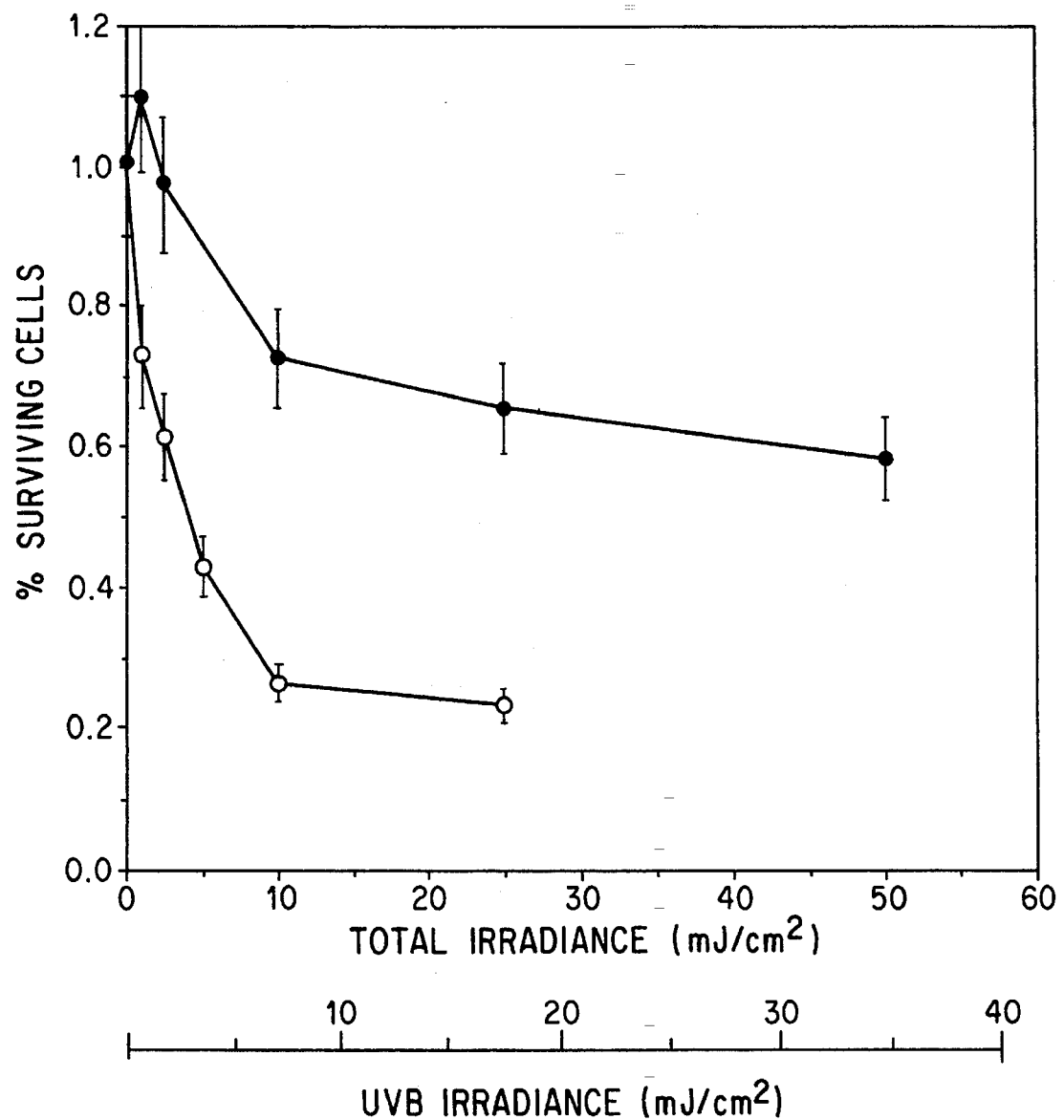
F I G. 4

TRANSGENIC ANIMAL MODEL SYSTEM FOR HUMAN CUTANEOUS MELANOMA

This is a continuation-in-part of U.S. Ser. No. 07/636,798, filed Jan. 2, 1991, (abandoned).

1. INTRODUCTION

The present invention relates to transgenic animal model systems for human cutaneous melanoma. It is based, at least in part, on the discovery that, in susceptible transgenic mice, accelerated formation of melanoma tumors occurred near the wound borders of skin grafts carrying the Tyr-SV40E transgene, indicating that factors present during wound healing facilitate the formation of cutaneous melanoma in susceptible tissue.

2. BACKGROUND OF THE INVENTION

2.1. MELANOMA

Primary malignant melanoma of the skin is the leading cause of death from any skin disease (see Fitzpatrick et al., 1983, in "Harrison's Principles of Internal Medicine," Edition, Petersdorf et al. eds., McGraw Hill, New York, pp. 836–838). Melanoma has been estimated to account for 1 percent of all skin cancers, with an incidence of approximately 4.5 in 100,000 person-years in Caucasians and 0.6 in 100,000 person years in Blacks in the U.S. (Ibid., p. 368). The incidence of melanoma is higher in light-skinned persons and increases with geographical proximity to the equator (Id.).

Because chemotherapy is frequently ineffective in treating melanoma, and because melanomas have a propensity for metastasis (Foos et al., 1983, in "Intraocular Tumors", eds. Lommatzsch et al., Springer-Verlag, Berlin pp. 51–57), early detection followed by surgical excision is a key element in successful treatment of the disease. The five-year survival decreases in proportion to the depth of tumor invasion (Id.). With less than 0.85 mm of invasion, the five year survival is about 99 percent; this drops to less than 10 percent in metastatic melanoma.

The incidence of melanoma has increased sharply over the last few decades. In the Connecticut Registry, between 1935 and 1939, the incidence of melanoma was $1.2/10^5$ persons/year; this increased to $4.8/10^5$ persons/year in 1965–1969, to $7.2/10^5$ persons/year in 1976–1977, and to $9/10^5$ persons/year in 1979–1980. By the year 2000, one in 90 Caucasians in the United States is expected to develop the disease (Rigel et al., 1987, J. Am. Acad. Dermatol. 17:1050–1053).

Melanomas are highly variable with respect to aberrant gene expression and chromosomal lesions but share a common characteristic of an acquired independence from environmental growth factors that are needed for proliferation of normal melanocytes (Halaban, 1991, Cancer Metastasis Rev. 10:129–140). In normal melanocyte proliferation as well as uncontrolled melanoma growth, receptors with tyrosine kinase activity, such as certain growth factor receptors, appear to play an important role (Id.; Becker et al., 1992, Oncogene 7:2303–2313). Various studies have suggested that a number of growth factors may be involved in melanomagenesis (Kock et al., 1991, Cancer Treat. Res. 54:41–66; Rodeck and Herlyn, 1991, Cancer Metastasis Rev. 10:89–101; Rodeck et al., 1991, J. Invest. Dermatol. 97:20–26); such growth factors include basic fibroblast growth factor (Albino et al., 1991, Cancer Res. 51:4815–4820; Rodeck and Herlyn, 1991, Cancer Metastasis Rev. 10:89–101; Dotto et al., 1989, J. Cell Biol. 109:3115–3128; contradicted by Yamanishi et al., 1992, Cancer Res. 52:5024–5029); transforming growth factors alpha and beta (Albino et al., 1991, Cancer Res. 51:4815–4820; Rodeck and Herlyn, 1991, Cancer Metastasis Rev. 10:89–101); hepatocyte growth factor/scatter factor (Halaban et al., 1992, Oncogene 7:2195–2206); tumor necrosis factor alpha and/or beta (Kirnbauer et al., 1992, J. Invest. Dermatol. 98:320–326; Krutmann et al., 1992, J. Invest. Dermatol. 98:923–928); platelet derived growth factor (Rodeck and Herlyn, 1991, Cancer Metastasis Rev. 10:89–101); and various interleukins (Kirnbauer et al., 1992, J. Invest. Dermatol. 98:320–326; partly contradicted by Lu et al., 1992, Proc. Natl. Acad. Sci. 89:9215–9219). Becker et al. (1992, Oncogene 7:2303–2313) implicates the fibroblast growth factor receptor in melanomagenesis. Other studies suggest that molecules that influence intracellular adhesion (Kirnbauer et al., J. Invest. Dermatol. 98:320–326; Krutmann et al., J. Invest. Dermatol. 98:923–928) or tissue protease activity (Mueller et al., 1992, Proc. Natl. Acad. Sci. U.S.A. 89:11832–11836) may be involved in the progression of human melanoma disease.

Thus, the literature is diverse and occasionally contradictory regarding the genesis and progression of melanoma. Furthermore, it is unclear what factors are involved in the initiation of events which lead to melanoma, as opposed to those operative in the progression of disease. A better understanding of the disease process could be obtained using a suitable animal model of human melanoma. The model could then also serve to test agents which might exacerbate the disease, and to test preventative or curative treatment strategies.

2.2. TRANSGENIC ANIMAL MODELS OF MELANOMA

Transgenic mice having an integrated recombinant gene comprised of the tyrosinase promoter and the simian virus 40 (SV40) early region containing transforming sequences (the "Tyr-SV40E" transgene, FIG. 1) which results in selective expression of SV40 large T ("T") and small t ("t") antigen genes in melanocytes and other pigmented cells, have been produced (Bradl et al., 1991, Proc. Natl. Acad. Sci. U.S.A.88:164–168; Klein-Szanto et al., 1991, Proc. Natl. Acad. Sci. U.S.A. 88:169–173; Bradl et al., 1991, Proc. Natl. Acad. Sci. U.S.A. 88:6447–6451; Larue et al., 1992, Proc. Natl. Acad. Sci. U.S.A. 89:9534–9538). Different lines of these mice were produced from the same inbred strain (C57BL/6) and are genetically identical except for the number of copies and chromosome site of integration characteristic of each line. Both ocular and cutaneous melanomas, and melanomas of various tissues, were found to develop in lines of these transgenic mice. The tumors were hypomelanotic and histopathologically similar to human melanomas (Id.). In general, mice of lines with larger numbers of transgene copies are highly susceptible and developed eye melanomas sooner than mice with smaller numbers of transgene copies and low susceptibility. Eye melanomas usually originated at a very young age, chiefly from the retinal pigment epithelium (see also Mintz and Klein-Szanto, 1992, Proc. Natl. Acad. Science U.S.A.89:11421–11425), in the high-copy lines. The eye tumors grew aggressively, were highly invasive, and metastasized to local as well as distant sites, often resulting in death before cutaneous melanoma could appear or become malignant (Bradl et al., 1991, Proc. Natl. Acad. Sci. U.S.A. 88:164–168).

In another transgenic animal model of melanoma, transgenic mice carry a metallothionein/ret ("MT/ret") fusion transgene, in which the inducible metallothionein-I promoter/enhancer was coupled to the ret oncogene (Iwamoto et al., 1991, EMBO 10:3167–3175). These mice are of mixed genetic background. Transgenic mouse lines carrying MT/ret exhibited widespread melanosis. In some lines, melanocytic tumors occurred, but these tumors differed from human melanoma in that they grew slowly and did not metastasize (Id.). A cell line developed from one such tumor was, however, able to metastasize after it was transplanted into immune-deficient (nude) mice (Taniguchi et al., 1992, Oncogene 7:1491–1496).

3. SUMMARY OF THE INVENTION

The present invention relates to transgenic animal model systems for human cutaneous melanoma which are superior to transgenic animal melanoma model systems known in the art in that the transgenic animals of the invention usually develop aggressive metastatic cutaneous melanomas, whereas the model systems of the prior art either (i) more frequently gave rise to lethal non-cutaneous melanomas which killed the animal before cutaneous melanoma could develop, or (ii) were non-malignant or malignant only after the cells were explanted in culture and then transferred into immune-deficient nude mice. Because most human melanomas are highly malignant cutaneous tumors, the present invention provides a model system which correlates much more closely with human disease.

The present invention is based, at least in part, on the discovery that, in Tyr-SV40E transgenic mice, frequent and accelerated formation of melanoma tumors occurred near the wound borders of skin grafts, thereby indicating that factors present during wound healing facilitate the formation of cutaneous melanoma in susceptible pigment cells. Accordingly, in various embodiments, the present invention provides for transgenic animal model systems for human cutaneous melanoma which reflect sequential stages of melanoma development and disease progression. These stages include (i) a melanocyte that is genetically susceptible to melanoma; (ii) excessive proliferation of such melanocytes; (iii) a non-malignant neoplasm arising from the genetically susceptible hyperplastic melanocyte; (iv) a malignant invasive melanoma developing from the neoplasm; and (v) metastatic melanoma resulting in dissemination of tumor beyond its primary site.

According to the invention, transgenic animals that are susceptible to cutaneous melanoma carry, as a transgene, a gene which creates a predisposition to melanoma, such as an oncogene or a gene encoding a growth factor or growth factor receptor, under the transcriptional control of a promoter specifically expressed in pigment cells. In further embodiments of the invention, animals exhibiting greater susceptibility to cutaneous melanoma, or more rapid progress of the disease, carry two or more such transgenes while retaining the same standard-strain background. A tendency to develop highly invasive and/or metastatic melanoma may be engineered in the melanoma-susceptible transgenic animals of the invention by further incorporating into such animals a transgene encoding, for example, a protein which increases proteolytic activity or an intercellular adhesion molecule.

Depending on the number or assortment of transgenes they carry, the transgenic animals of the invention may be used as models of either a human who is genetically susceptible to cutaneous melanoma, a genetically susceptible human who has been subjected to an environmental risk-factor (e.g. a severe sunburn), or a genetically susceptible human who exhibits multiple nevi, has developed malignant melanoma, or suffers from metastatic melanoma.

The transgenic animals of the invention, or cell lines derived therefrom, may be used as models of human cutaneous melanoma for the development of new anti-melanoma therapies and diagnostics.

4. DESCRIPTION OF THE FIGURES

FIG. 1. Map of Tyr-SV40E. The open box represents 5' flanking sequence of the mouse tyrosinase gene. Major and minor transcription initiation sites are indicated by the solid and dashed arrows, respectively. The SV40 early region, which includes the coding region for the large T and small t tumor antigen genes, is indicated by the hatched box (kb=Kilobases).

FIGS. 2a–2f. Development of melanoma following grafting of skin from a transgenic mouse donor that is highly susceptible to melanoma and will die young of eye melanoma onto a transgenic mouse host of a line exhibiting low susceptibility to melanoma. The most advanced lesions shown here arise by 10–11 months after grafting. (a) Arrows pointing to pigmented macules outlining graft border. (b) Arrows pointing to rips in thin tissue at graft border. (c) Smaller arrow pointing to a small pigmented nevus in the central region of the graft; larger arrow pointing to larger nevus spreading into the graft from the edge. (d) The same graft as in (c) shown two weeks later; smaller arrow pointing to the central nevus and larger arrow pointing to the ulcerated invasive advanced melanoma developed from the spreading lesion in (c). (e) In another case, arrow pointing to ulcerated advanced melanoma. (f) In another case, the melanoma has spread through the entire graft site.

FIGS. 3a–3h. Histology of progressive changes leading to melanoma arising in the graft. (a) Low magnification section with part of melanoma (at left) showing invasion and ulceration of skin surface, an earlier stage of dense associated cells with little pigment, and a still earlier stage of a small macule populated with highly pigmented cells (e.g. at arrows, left to right). (b) Slightly enlarged view of panel (a) from region at right-hand arrow (note the cluster of darkly pigmented cells). (c) Similar enlargement of panel (a) from region of middle arrow showing large cluster of hypopigmented transformed cells. (d) Enlarged view of panel (a), left-arrow region, showing lobulated tumor. (e) Enlarged section of tumor showing invasion of underlying muscle and connective tissue (at lower region of panel). (f) Section of tumor metastasis to lymph node. (g) Tumor metastasis to lung. (h) Enlargement of the same tumor metastasis in lung.

FIG. 4. Comparative cytoxicity of ultraviolet B light (UVB) for wild-type C57BL/6 melanocytes (●) and for transgenic C57BL/6 melanocytes from mice with the Tyr-SV40E transgene (o). The transgenic cells were tested at culture passages at which they differed from normal cells (in having shorter doubling time and less melanin) but were not tumorigenic. The UVB component (280–320 nm) is 70% of the total irradiance reaching the cells. The wild-type cells were less sensitive to UVB at all intensities tested. Each point represents at least three independent measurements. Error bars indicate ±3 SE.

Figure 5:
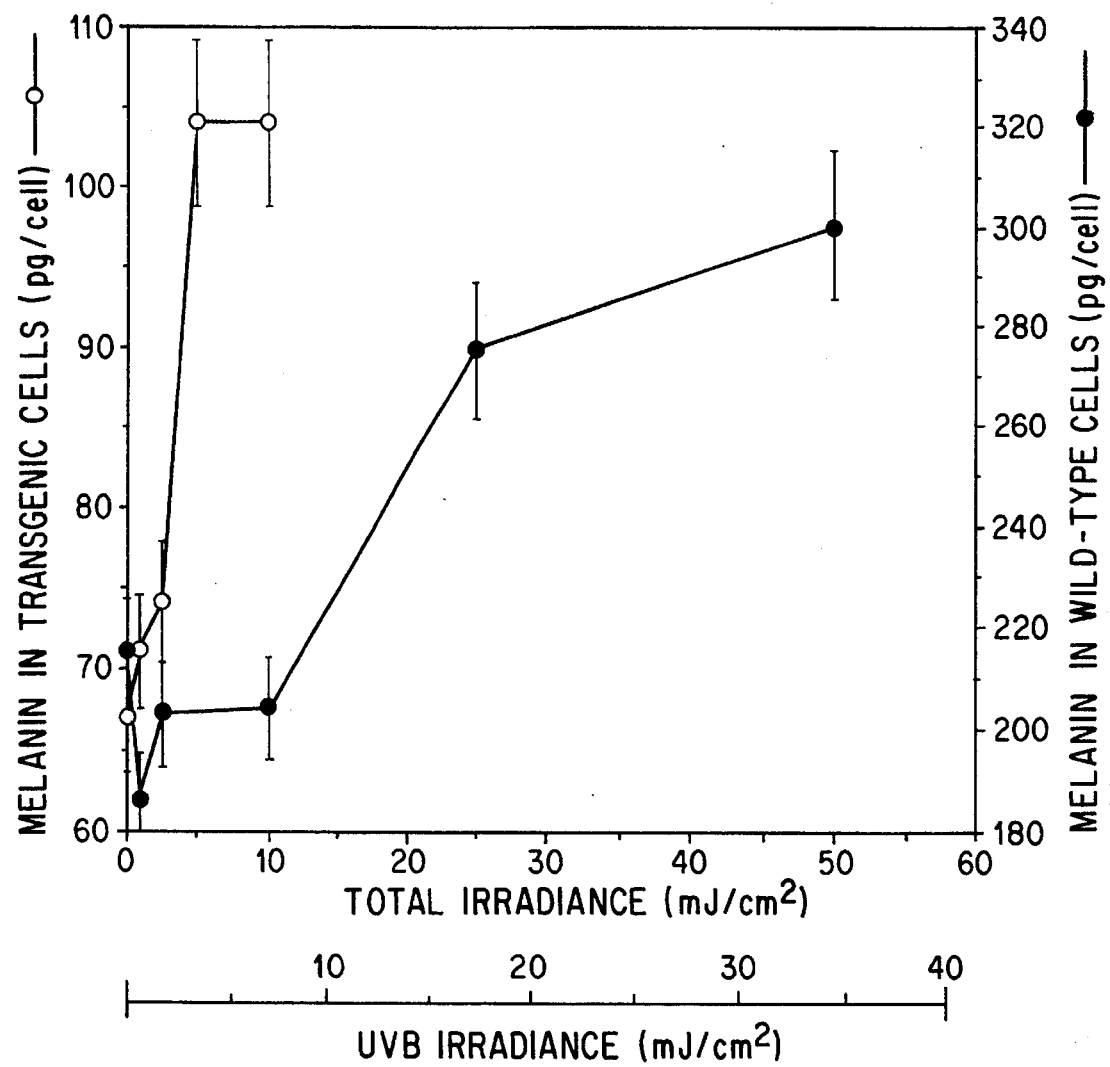

FIG. 5. Induction of melanization 24 hr after exposure to UVB in the same wild-type (●) and transgenic (o) melanocytes as shown in FIG. 4 (with omission here of the last transgenic-cell observation in FIG. 4). At the lowest intensities measured, melanin was greatly increased in the transgenic cells. At least three independent measurements were made for each point. Error bars indicate ±3 SE.

Figure 6A:
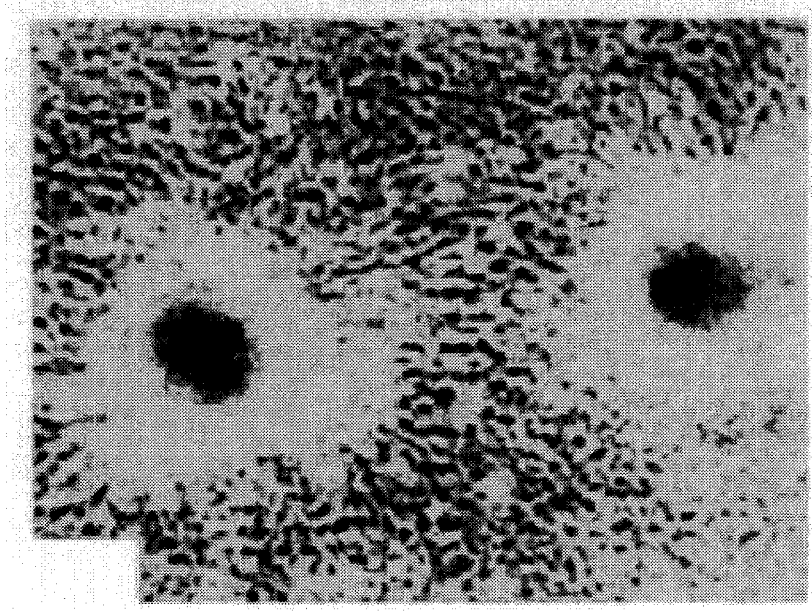
Figure 6B:
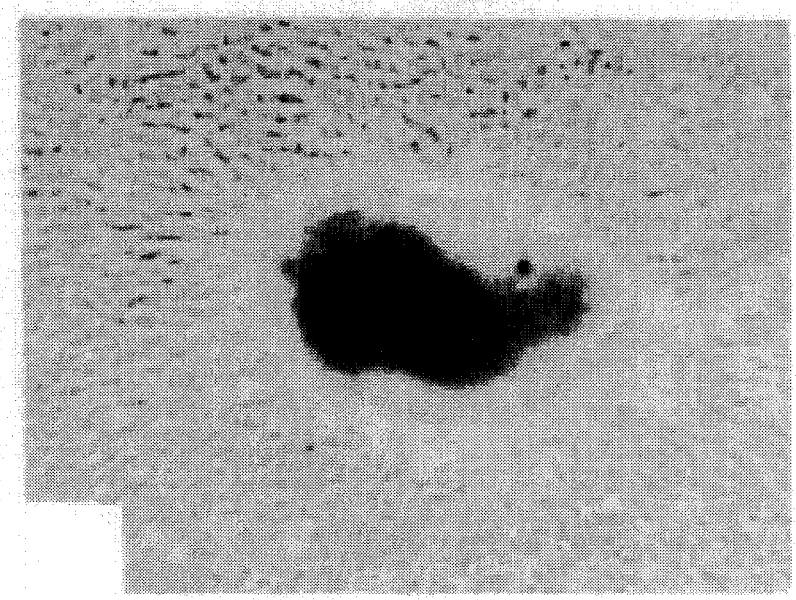
Figure 6C:
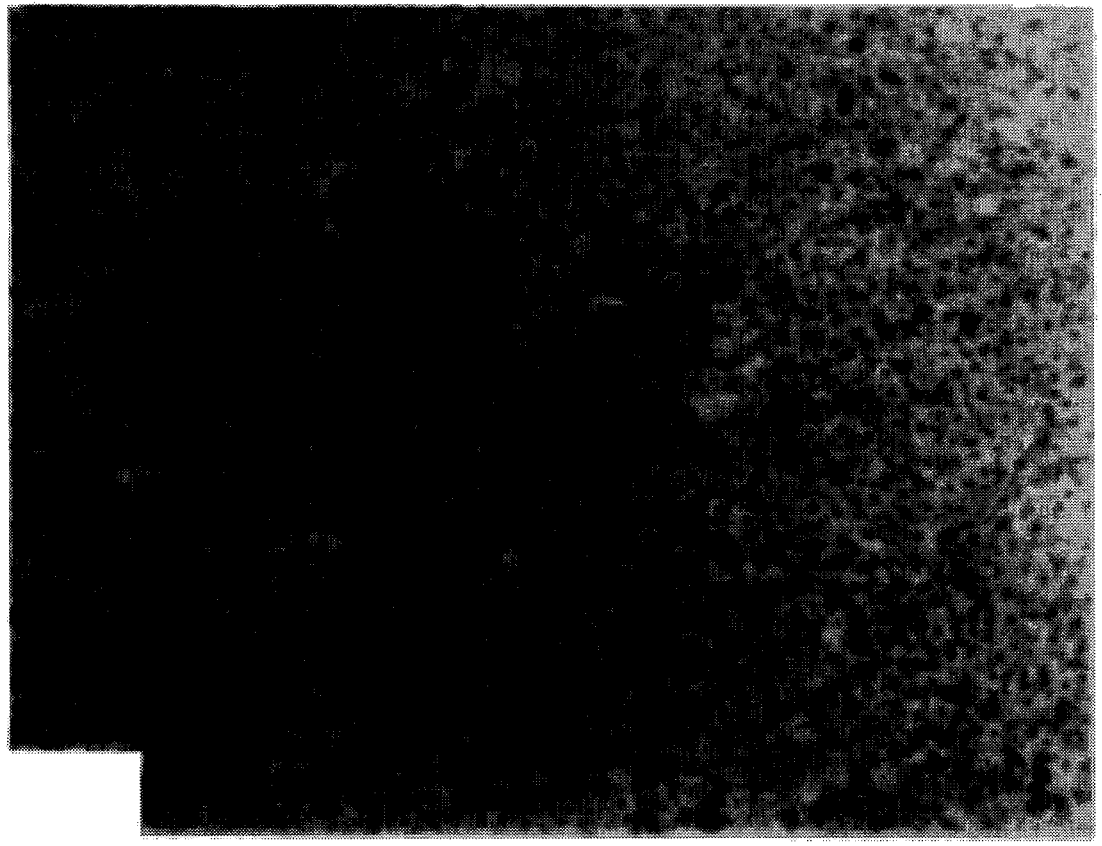

FIGS. 6a–6c. (a) Transgenic cultured melanocytes formed foci at confluence after exposure to 0.7 mJ/cm$^2$ of UVB irradiation, but cells from the foci were not tumorigenic. (b) After 1.75 mJ/cm$^2$ of UVB, the foci that formed were generally larger and thicker; the cells grown from them were tumorigenic. (c) Wild-type melanocytes did not form foci after 1.75 mJ/cm$^2$ of UVB.

Figure 7:
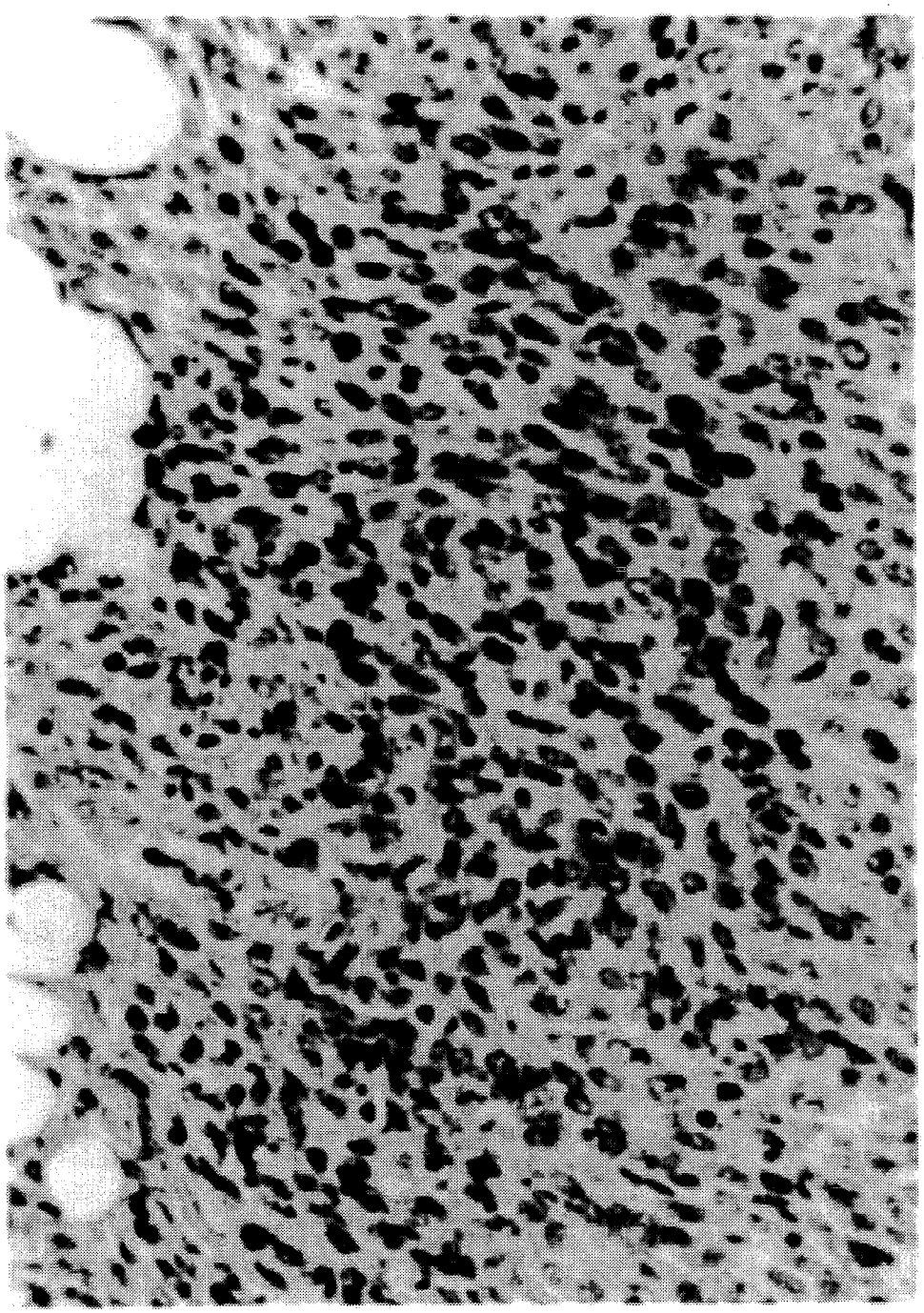

FIG. 7. Characteristic relatively undifferentiated amelanotic melanoma, with a mixture of spindle and epithelioid cells, formed in an athymic host after subcutaneous inoculation of transgenic melanocytes from foci due to 1.75 mJ/cm$^2$ of UVB radiation. The cells have invaded neighboring adipose tissue (top). (Hematoxylin/eosin stain; ×140).

5. DETAILED DESCRIPTION OF THE INVENTION

The present invention relates to model systems for human cutaneous melanoma.

According to the invention, transgenic animals are produced which reflect the various stages of melanoma development and disease progression. Experiments described in Sections 6 and 7, infra illustrate that genetic susceptibility to melanoma is but one step in cutaneous melanoma development. Other factors interplay with genetic susceptibility to result in melanoma formation and progression to metastatic disease. The transgenic animals of the invention recreate the clinical course of human cutaneous melanoma like successive frames of a motion picture film.

A melanocyte in the skin of a person who is genetically susceptible to melanoma may be considered to be the first enabling stage of human cutaneous melanoma development. This stage is represented, according to the invention, by a transgenic animal carrying, as a transgene, a gene which creates a predisposition to melanoma under the transcriptional control of a pigment cell-specific promoter. Such animals are referred to herein as "melanoma-susceptible transgenic animals." Examples of categories of genes which may confer such a predisposition include, but are not limited to, oncogenes or genes encoding growth factors, growth factor receptors, or other genes involved in cell or tissue repair.

The next stage of human cutaneous melanoma development may arise when the genetically susceptible individual is subjected to a risk factor, such as exposure to sunlight leading to a severe sunburn. According to the present invention, transgenic animal models representative of this stage may be produced by either (i) subjecting a melanoma-susceptible transgenic animal to a similar risk factor (for example, by creating a wound in the animal or by exposing the animal to ultraviolet light or to a carcinogen; see Sections 6 and 7, infra) or (ii) engineering a transgenic animal that carries not only a transgene that confers susceptibility to melanoma but also a transgene encoding a product that facilitates melanoma formation.

As discussed in detail in Section 6, infra, when skin from a C57BL/6 mouse carrying the Tyr-SV40E transgene (FIG. 1) that was highly susceptible to melanoma was grafted onto a C57BL/6, Tyr-SV40E-bearing transgenic mouse that exhibited low susceptibility to melanoma, it was discovered that the rate of nevus and melanoma formation at the borders of the graft itself far exceeded the rate of nevus/melanoma formation at the graft center. Thus, although the entire skin graft was genetically susceptible to melanoma formation, nevi and tumors formed preferentially at the graft borders, where wound-healing factors (e.g. growth factors, molecules involved in cell or tissue repair, etc.) were present at relatively high concentrations. According to the invention, transgenes encoding such factors (or their receptors) may be used to facilitate melanoma formation in genetically susceptible animals.

For example, a transgenic animal that is genetically susceptible to melanoma by virtue of an oncogene transgene may be mated to a separately produced transgenic animal of the same background strain carrying a gene encoding a wound-healing growth factor; their doubly transgenic offspring may be used as models of a melanoma-susceptible person exposed to a risk factor. Animals of increasing risk, with multiple transgenes, may be produced by engineering such animals to carry genes encoding multiple wound-healing factors, factor receptors, etc.

Nevi which develop in transgenic animals of the invention may be used as models of human nevi; cutaneous melanomas which develop in transgenic animals of the invention may be used as models of human cutaneous melanoma.

In its later stages, human cutaneous melanoma is an invasive and frequently metastatic disease. According to the present invention, a transgenic animal model of invasive and/or metastatic melanoma may be produced without grafting or wounding skin by engineering a melanoma-susceptible animal, as described supra, to further carry a transgene(s) encoding a protein that promotes proteolysis (and thereby facilitates invasion into contiguous tissue; e.g. tissue plasminogen activator) and/or a protein involved in cell-to-cell interactions (e.g. intercellular adhesion protein-1, ICAM-1).

In still further embodiments of the invention, endogenous genes encoding growth factor(s), growth factor receptor(s), cytoskeletal structural element(s), and/or intercellular adhesion molecule(s) may be "knocked out" by insertional mutation or homologous recombination in embryo cells from which melanoma-susceptible transgenic animals are generated. A decrease in melanoma formation in such animals would suggest that the product of the inactivated gene is material to the origin or progression of melanoma.

In additional embodiments, melanocytic cell lines may be prepared from skin of transgenic animals of the invention and used as models of progressive genetic changes leading to human cutaneous melanoma.

For purposes of clarity of description and not by way of limitation, further detailed description of the invention has been divided into the following subsections:

(i) preparation of melanoma-susceptible transgenic animals;

(ii) crossbreeding transgenic animals of the invention to produce further melanoma-susceptible animals;

(iii) "wound-induced" transgenic animal models of human cutaneous melanoma;

(iv) "knock-out" mutations;

(v) cell lines; and (vi) use of transgenic animal model systems to study melanoma.

5.1. PREPARATION OF MELANOMA-SUSCEPTIBLE TRANSGENIC ANIMALS

The present invention provides for transgenic animals that are, as set forth above, genetically susceptible to melanoma due to the presence of one or more transgene(s) encoding (a) an oncogene; (b) a growth factor; (c) a growth factor receptor; and/or (d) any other protein involved in cell or tissue repair. As the term is used herein, "susceptibility" to melanoma refers to a proclivity to give rise to melanoma in which the incidence of melanoma is significantly increased relative to normal animals. The actual development of melanoma in the susceptible transgenic animals may, with reasonable frequency, occur under natural conditions, but may alternatively require exposure to wound-healing conditions or to an agent such as ultraviolet light or a carcinogen.

The present invention further provides for melanoma-susceptible transgenic animals that are further engineered to carry a transgene(s) encoding a protein that promotes proteolysis or that is involved in cell-to-cell interactions, so as to provide a transgenic animal model for invasive/metastatic melanoma.

More detailed descriptions of the transgenic animals described supra, including multiply transgenic animals, are set forth below. Such transgenic animals may be tested so as to ascertain susceptibility to melanoma according to the invention.

According to the present invention, transgenic animals of any non-human species, including but not limited to mice, rats, rabbits, guinea pigs, pigs, or non-human primates may be produced using any technique known in the art, including but not limited to microinjection, electroporation, cell gun, cell fusion, microinjection of teratocarcinoma stem cells or functionally equivalent (see Mintz et al., 1978, Proc. Natl. Acad. Sci. U.S.A. 75:2834–2838) embryonic stem cells into embryos, or aggregation with embryo cells; DEAE - dextran, etc. (see Mintz, 1962, Am. Zoologist 2:432; Mintz, 1967, Proc. Natl. Acad. Sci. U.S.A. 58:344–351; Mintz and Illmensee, 1975, Proc. Natl. Acad. Sci. U.S.A. 72:3585–3589; Jaenisch and Mintz, 1974, Proc. Natl. Acad. Sci. U.S.A. 71:1250–1254; Wagner and Mintz, 1982, Mol. Cell. Biol. 2:190–198). In preferred embodiments of the invention, transgenic animals may be generated according to the method set forth in Wagner et al., 1981, Proc. Natl. Acad. Sci. USA 78:5016–5020, which is incorporated by reference in its entirety herein. Briefly, this method entails the following. Transgenic offspring may be prepared by microinjecting a recombinant nucleic acid construct into fertilized eggs. For example, and not by way of limitation, fertilized mouse eggs may be collected, for example, from recently mated females with vaginal plugs, and then microinjected with construct DNA by a modification of the procedure described in Lin et al., 1966, Science 151:333. Construct DNA, at a concentration of about 0.01 ug/ml, may be microinjected into the male pronucleus of fertilized eggs, in an amount such that the volume of the pronucleus approximately doubles. The injected eggs may then be transferred to female mice which had been mated the night before to vasectomized males. See also U.S. Pat. No. 4,873,191 by Wagner and Hoppe.

The present invention provides for transgenic animals which carry the transgene in all their cells as well as animals which carry the transgene in some, but not all cells, which are said to be cellular mosaic animals.

The present invention further provides for inbred successive lines of transgenic animals carrying relevant transgenes that offer the advantage of providing a virtually homogeneous genetic background. A genetically homogeneous line of animals provides a functionally reproducible tumor model system; a genetically heterogeneous line of animals may exhibit inconsistency due to the interaction of the product of the gene of interest with other gene products that may vary among animals due to gene segregation in the progeny.

The term "line" should be herein construed to refer to a group of genetically related animals descended from one genetically altered individual and comprising at least one male animal and one female animal which are capable of reproduction, and refers to parental animals as well as successive generations of their progeny.

To produce a virtually genetically homogenous line of animals according to the invention, it is desirable to use animals which are themselves members of an inbred, fully characterized strain to generate transgenics. In certain embodiments of the invention, it may be particularly advantageous to use a strain of animals which are known to exhibit a particular characteristic, for example, but not by way of limitation, animals which have an augmented or deficient immune response, or animals which exhibit particular pigmentation characteristics, such as highly pigmented animals, albino animals, patterned animals, or animals whose pigmentation can be altered. For example, in a specific, non-limiting example of the invention, a transgenic mouse carrying a construct comprising the tyrosinase gene under the control of the mouse metallothionein promoter, as described in Larue and Mintz, 1990, Somatic Cell. and Mol. Genet. 16:361–368, may be engineered to carry transgenes according to the invention; such animals, which have pigment cells chiefly dispersed in the skin rather than, as in wild-type mice, chiefly clustered in hair follicles, may offer the advantage of having a greater number of targets for melanoma formation.

In another specific, preferred embodiment of the invention, an inbred line of transgenic animals may be produced as follows. A relevant transgene may be introduced into animals of a genetically homogeneous strain such as, but not limited to, C57BL/6. Transgenic animals which carry the recombinant construct may be identified by Southern blot analysis of DNA prepared from a biopsy of tail, ear, toe, or any other appropriate source of cells or tissue; this analysis should also indicate the number of integration sites and the number of transgene copies linked in tandem at a single site. For the construction of a homogeneous line of animals, it is desirable to use, as founders, animals having only one transgene integration site into which one or, preferably, tandem copies of the transgene have been inserted. The phenotype of these animals may be evaluated as they mature.

Transgenic animals which exhibit a desirable phenotype may then be bred with a non-transgenic member of the original strain (e.g. C57/BL/6) to produce progeny which carry the transgene superimposed on a common genetic background. Progeny which carry the appropriate genotype may be evaluated by Southern blot analysis of DNA (see above) or by phenotype. Appropriate transgenic progeny may then be interbred or bred with the original transgenic parent to increase the number of animals of both sexes available for breeding purposes. By continuing to interbreed animals with the same genotype with respect to the transgene and otherwise, a virtually genetically homogeneous line of animals may be produced. If animals heterozygous for the transgene are crossed, their progeny should comprise 25% homozygotes, 50% heterozygotes, and 25% wild-type offspring with respect to the transgene. Homozygotes will be likely to contain a higher concentration of transgene product than heterozygotes. If the transgene is an oncogene leading to melanoma-susceptibility, homozygous animals may exhibit a greater susceptibility to melanoma. In certain circumstances, homozygous animals may not survive long enough to produce offspring, and the line of animals may be perpetuated by heterozygotes, or ovaries from a homozygous or heterozygous transgenic animal may be grafted to the ovarian capsule of non-transgenic animals by standard techniques (Palm, 1961, in "Transplantation of Tissues and Cells," Billingham and Silvers, eds., Wistar Instit. Press, Philadelphia, pp. 49–56).

Although the present invention is not so limited, it is desirable that the transgenes of the invention comprise a promoter/enhancer element which is directly or indirectly selectively active in pigment cells and more preferably specifically active in pigment cells. The tyrosinase promoter exemplifies a promoter sequence which is directly active in pigment cells (Ruppert et al., 1988, EMBO J. 7: 2715–2722). Promoter sequences which are effective include inducible promoters, even if not tissue-specific, as well as promoters which require activation by a transactivating element or which reversibly bind to a repressor element, and include, but are not limited to the metallothionein promoter (Brinster et al., 1982, Nature 296: 39–42) and HIV-LTR (Valerie et al., 1988, Nature 333: 78–81).

In alternative embodiments of the invention, directly and non-specific or indirectly active promoters may be used together in the same construct. For example, and not by way of limitation, a gene of interest may be placed under the control of an ultraviolet light-inducible promoter, such as the UV-activated promoter in the human immunodeficiency virus long terminal repeat (Valeri et al., 1988, Nature 333:78–81) as well as the tyrosinase promoter. When such a construct exists as a transgene in a transgenic animal, exposure of the animal to ultraviolet light may be used to increase the expression of the gene of interest beyond the level associated with tyrosinase promoter activity alone. If the gene of interest is an oncogene, such a transgenic animal may serve as an inducible model for melanoma formation in humans. An inducible melanoma model system would offer the advantage of allowing for control of the initiation of oncogenesis thereby permitting avoidance of the early mortality observed in some transgenic animals. An ultraviolet light-inducible melanoma model may be used to favor the development of skin tumors rather than eye tumors; for example, the transgenic animals may be exposed to UV light with their eyes shielded or when they are young and their eyes are still closed.

5.1.1. TRANSGENIC ANIMALS CARRYING AN ONCOGENE TRANSGENE

Melanoma-susceptible transgenic animals of the invention include transgenic animals that carry an oncogene transgene. Preferably, the transcription of this oncogene is controlled by a pigment-cell-specific promoter, so as to avoid tumor formation in other tissues which may detract from the validity of the system as a model of melanoma. In most preferred embodiments, the promoter is the tyrosinase promoter.

The oncogene may be any known viral or non-viral oncogene, including but not limited to SV40 T antigen or t antigen, src, fps, res, yes, fgr, ros, abl, ski, erb A, erb B, fms, fos, mos, sis, myc, myb, rel, neu, ret, kit, raf, H-ras, K-ras, jun, adenovirus E1A, and ets. In certain embodiments it is preferred that the oncogene exhibit tyrosine kinase activity. In a non-limiting, specific, preferred embodiment of the invention, the transgene is Tyr-SV40E (FIG. 1).

5.1.2. TRANSGENIC ANIMALS CARRYING A TRANSGENE ENCODING A GROWTH FACTOR

Melanoma-susceptible transgenic animals of the invention include transgenic animals that carry a transgene encoding a growth factor, in which transcription is preferably controlled by a pigment cell-specific promoter, and most preferably controlled by the tyrosinase promoter.

The transgene may encode any growth factor related to wound healing, including, but not limited to, basic fibroblast growth factor, acidic fibroblast growth factor, transforming growth factor alpha, transforming growth factor beta, keratinocyte growth factor, platelet derived growth factor alpha or beta, hepatocyte growth factor/scatter factor, mast cell growth factor, interferon gamma, interleukin-1, interleukin-6, interleukin-7, tumor necrosis factor alpha, tumor necrosis factor beta, melanoma growth stimulating activity or epidermal growth factor. In certain embodiments it is preferred that the growth factor has potential autocrine as well as paracrine activity and, in additional preferred embodiments, that the growth factor interacts with a receptor that has tyrosine kinase activity.

5.1.3. TRANSGENIC ANIMALS CARRYING A TRANSGENE ENCODING A GROWTH FACTOR RECEPTOR

Melanoma-susceptible transgenic animals of the invention include transgenic animals that carry a transgene encoding a growth factor receptor, in which transcription is preferably controlled by a pigment cell-specific promoter, and most preferably controlled by the tyrosinase promoter.

The transgene may encode any receptor associated with a growth factor related to wound healing, including, but not limited to, receptors for fibroblast growth factor (acidic or basic), transforming growth factor (alpha or beta), keratinocyte growth factor, platelet derived growth factor alpha or beta, hepatocyte growth factor/scatter factor, mast cell growth factor, interferon gamma, interleukin-1, interleukin-6, interleukin-7, tumor necrosis factor (alpha or beta), melanoma growth stimulating activity or epidermal growth factor. In preferred embodiments of the invention, the growth factor receptor has tyrosine kinase activity.

5.1.4. TRANSGENIC ANIMALS CARRYING A TRANSGENE ENCODING A PROTEIN INVOLVED IN CELL OR TISSUE REPAIR

Melanoma-susceptible transgenic animals of the invention include transgenic animals that carry a transgens encoding a protein involved in cell or tissue repair, in which transcription is preferably controlled by a pigment cell-specific promoter, most preferably, the tyrosinase promoter. For example, and not by way of limitation, such proteins include proteins associated with DNA repair, the immune response (including the interferons and interleukins), and structural proteins.

5.1.5. TRANSGENIC ANIMALS THAT ARE MODELS OF INVASIVE/METASTATIC MELANOMA

5.1.5. TRANSGENIC ANIMALS CARRYING A TRANSGENE ENCODING A PROTEIN THAT PROMOTES INVASION OR PROTEOLYSIS

The present invention, in particular embodiments, provides for melanoma-susceptible transgenic animals as described supra that further carry a transgens encoding a protein that directly or indirectly promotes proteolysis, in which transcription is preferably controlled by a pigment cell-specific promoter, and most preferably controlled by the tyrosinase promoter. Such proteins include, but are not limited to, tissue plasminogen activator, urokinase plasminogen activator, tissue factor (as described in Mueller et al., 1992, Proc. Natl. Acad. Sci. U.S.A. 89:11832–11836), collagenases, cathepsin, stromelysin, etc.

Such transgenic animals may exhibit a propensity to develop particularly invasive forms of melanoma.

5.1.5.2. TRANSGENIC ANIMALS CARRYING A TRANSGENE ENCODING A PROTEIN INVOLVED IN CELL SHAPE OR INTERCELLULAR ADHESION

The present invention, in particular embodiments, provides for melanoma-susceptible transgenic animals as described supra that further carry a transgene encoding a protein that is involved in cell shape or intercellular adhesion, in which transcription is preferably controlled by a pigment cell-specific promoter, and most preferably controlled by the tyrosinase promoter. Such proteins include, but are not limited to, intercellular adhesion protein-1 (ICAM-1) and non-erythrocytic spectrin.

Such transgenic animals may exhibit a propensity to develop metastatic melanoma.

5.2. CROSSBREEDING TRANSGENIC ANIMALS OF THE INVENTION TO PRODUCE FURTHER MELANOMA-SUSCEPTIBLE ANIMALS

In further embodiments of the invention, one type of melanoma-susceptible transgenic animal as described in sections 5.1.1.–5.1.5. may be mated to either (i) a second type of transgenic animal as described in sections 5.1.1.–5.1.5.; or (ii) a non-transgenic animal that carries a non-wild-type allele that results in increased expression of an oncogene, growth factor, growth factor receptor, protein involved in cell or tissue repair, protein that promotes proteolysis or protein involved in intercellular adhesion as described in sections 5.1.1.–5.1.5. As discussed Supra, the offspring of these matings, transgenic animals carrying multiple genes which may be associated with melanoma, may serve as models of a human who is genetically susceptible to melanoma and has been exposed to conditions which facilitate melanoma development and/or progression.

For example, and not by way of limitation, a transgenic animal carrying an oncogene transgene may be mated to a transgenic animal carrying a transgene encoding a growth factor, or a transgenic animal carrying a transgene encoding a first growth factor may be mated to a transgenic animal carrying a transgene encoding a second growth factor. Further, a doubly transgenic animal so produced may be mated to an additional transgenic animal to produce triply transgenic animals, which may in turn be mated to other transgenic animals, and so forth in order to produce animals that carry a multiplicity of transgenes and which thus exhibit a range of susceptibility to melanomas and may be used as models of the various stages of melanoma development and progression set forth above.

Additionally, such multiply transgenic animals carrying more than one type of transgene may be produced by coinjecting (or otherwise introducing) multiple transgenes into the fertilized egg or embryo.

Alternatively, a naturally occurring (i.e. non-transgene) non-wild-type allele may be introduced, by breeding, into a transgenic line of animals by mating a transgenic animal according to sections 5.1.1.–5.1.5. to a non-transgenic animal carrying the allele. Such alleles lead to overproduction of an oncogene, growth factor, growth factor receptor, protein involved in cell or tissue repair, protein that promotes proteolysis, or protein involved in intercellular adhesion or adhesion to stromal or basement membrane components such as laminin or fibronectin.

5.3. "WOUND-INDUCED" TRANSGENIC ANIMAL MODELS OF HUMAN CUTANEOUS MELANOMA

In further embodiments of the invention, wound-healing conditions are created in a tissue of a melanoma-susceptible transgenic animal in order to produce a model of a genetically susceptible human who has been exposed to conditions which facilitate melanoma development and/or progression. In certain preferred embodiments, the wound-healing conditions are created by grafting skin from a highly melanoma-susceptible donor onto a low-susceptibility immunecompatible transgenic host (see infra); this technique is particularly useful if the highly melanoma-susceptible animal may be expected to succumb to non-cutaneous disease prior to the formation of cutaneous tumor. In additional embodiments of the invention, a wound may be created in a melanoma-susceptible animal so as to promote tumor formation. All such wounds should be produced using sterile surgical technique and adequate anesthesia.

For the purpose of skin grafting, it is desirable to graft a portion of skin from a melanoma-susceptible donor animal onto a low-susceptibility immune-compatible transgenic host. The term "low susceptibility" refers to an incidence of melanoma that is lower than that exhibited by the skin donor. "Immune-compatible," as used herein, indicates that the immune system of the host does not reject the donor tissue. For example, two lines of transgenic animals are immune-compatible if they both are created from the same homogeneous inbred strain and therefore differ only in transgene location, copy number, expression, and phenotype conferred. As an illustrative example, founders of two transgenic mouse lines may both be derived from a C57BL/6 mouse, but one founder ("A") carries four copies of transgene X on chromosome 6 and the founder of the other line ("B") carries one copy of transgene X on chromosome 7. "A" is likely to be melanoma-susceptible, whereas "B" is not. But other pairs of transgenic animals may be immune-compatible that carry different transgenes. For example, a melanoma-susceptible transgenic mouse ("C") which serves as skin donor may be derived from the C57BL/6 strain and carry the SV40 T antigen gene under the control of the tyrosinase promoter, and an immune-compatible transgenic mouse ("D") which serves as host may be derived from the C57BL/6 strain and carry the SV40 T antigen gene minus the nuclear localization sequence under the control of the tyrosinase promoter. This host "D" should exhibit little or no propensity to develop melanoma, but should not be expected to reject tissue from "C", which bears trace amounts of cell surface T antigen.

Similarly, low susceptibility animals carrying a transgene that confers susceptibility to melanoma may desirably express low levels of transgene product. The purpose of selecting, as a host animal, a transgenic animal that exhibits low susceptibility to melanoma is simply to provide a host that will not reject the melanocytes in the grafted tissue but will survive for a period of time sufficient to allow the formation of cutaneous melanoma. Experiments have indicated that when the transgene is not expressed endogenously in the non-transgenic strain, some level of expression of transgene by the host may be necessary: for example, when donor skin from a C57BL/6-Tyr-SV40E transgenic mouse was grafted onto a C57BL/6 non-transgenic host, melanocytes in the graft were selectively destroyed by the host immune system.

However, if the transgene product is endogenously expressed by the strain from which the transgenic melanoma-susceptible animal is derived, then the low susceptibility host may be a non-transgenic animal. For example, if the melanoma-susceptible transgenic animal is derived from a C57BL/6 mouse and its transgene results in overproduction of an endogenous growth factor (e.g. platelet derived growth factor), then a non-transgenic C57BL/6 mouse may be used as a host for skin grafting.

When the skin-grafting technique is used, it is desirable for the host to be young enough so that they have not yet attained their full adult size. The graft will then continue to grow with the host. In an adult mouse there are very few mitoses of skin melanocytes. With ongoing growth of the grafted skin, melanocytes may resume division and provide targets for melanoma formation. Any standard method of skin-grafting may be utilized.

In a preferred, specific non-limiting embodiment of the invention, which illustrates the general method, skin from a melanoma-susceptible transgenic animal donor carrying the Tyr-SV40E transgene may be grafted onto a low-susceptibility Tyr-SV40E host transgenic animal. The degree of susceptibility of both animals is predictable if the donor comes from a genetically homogeneous line of transgenic animals that exhibit high susceptibility to melanoma and the host comes from a genetically homogeneous line of transgenic animals that exhibit low susceptibility to melanoma. An area of full-thickness skin up to approximately 12 mm in diameter may be excised from the donor and then placed on a graft bed of slightly larger size cleared of skin on the host. The graft may then be sprinkled with a small amount of antibiotic-containing powder such as nitrofurazone, overlaid with petroleum jelly impregnated gauze, and then wrapped in place with a plaster bandage.

Because one use of the model systems of the invention is to test the ability of agents to induce melanoma formation, it may sometimes be desirable to use, as graft, skin that contains areas of cells that express the transgene and other areas that express it much less or not at all, and which serve as a control. For example, in certain lines of transgenic mice, expression of a transgene can characteristically vary in a single animal, producing areas of skin in which the transgene expression is very high and other areas in which the transgene is expressed at a very low level (due to clonal variation in gene expression; Bradl et al., 1991, Proc. Natl. Acad. Sci. U.S.A. 88:6447–6451). The areas of high transgene expression are markedly hypomelanotic, so that boundaries of high and low expression can be recognized by differences in pigmentation. It may be desirable to choose an area of skin for grafting which contains such a boundary. In such embodiments, the graft contains an internal control reflecting different levels of susceptibility.

In additional embodiments of the invention, a wound may be created in a melanoma-susceptible animal in order to facilitate melanoma formation. Such a wound may consist of a single cut, or may be in a simple intersecting pattern of cuts that results in some areas of greater wounding. Such cuts should penetrate the full thickness of the skin. Wounds may also be blisters caused by exposure to ultraviolet light. Some local wounding may also be produced by abrasion or by corrosive chemicals.

In an additional embodiment of the invention, melanocytes (or mixtures of melanocytes and other cells) harvested from a highly melanoma-susceptible transgenic animal donor and expanded in culture may be injected (e.g. using a conventional hypodermic needle or trochar) intradermally and/or subcutaneously into a low-susceptibility immune-compatible transgenic animal, and the injection site subsequently evaluated for melanoma formation. Alternatively, such cells may be injected into a weal raised in the host animal.

5.4. "KNOCK-OUT" MUTATIONS

In further embodiments of the invention, it may be desirable to study the effect of genetically engineered mutations that "knock-out" or inactivate genes in the categories set forth in section 5.1. supra, to determine whether the knock-out alters susceptibility to melanoma. Such knock-outs may be achieved, for example, by established techniques of homologous recombination applied, in this case, to embryonal stem cells from embryos of transgenic mice.

For example, and not by way of limitation, knockout mutations of interest may decrease or eliminate expression of the following genes: SV40 T antigen or t antigen, src, fps, fes, yes, fgr, ros, abl, ski, erb A, erb B, fms, fos, mos, sis, myc, myb, rel, neu, ret, kit, raf, H-ras, K-ras, jun, adenovirus E1A, and ets, genes encoding basic fibroblast growth factor, transforming growth factor alpha, transforming growth factor beta, keratinocyte growth factor, platelet derived growth factor alpha or beta, hepatocyte growth factor/scatter factor, mast cell growth factor, interferon gamma, interleukin-1, interleukin-6, interleukin-7, tumor necrosis factor alpha, tumor necrosis factor beta, melanoma growth stimulating activity or epidermal growth factor; receptors for fibroblast growth factor (acidic or basic), transforming growth factor (alpha or beta), keratinocyte growth factor, platelet derived growth factor alpha or beta, hepatocyte growth factor/scatter factor, mast cell growth factor, interferon gamma, interleukin-1, interleukin-6, interleukin-7, tumor necrosis factor (alpha or beta),-melanoma growth stimulating activity or epidermal growth factor; intercellular adhesion molecule ICAM-1; tissue plasminogen activator, and tissue factor (as described in Mueller et al., 1992, Proc. Natl. Acad. Sci. U.S.A. 89:11832–11836).

Analogous to "knock-out" mutations created by genetic engineering, naturally occurring mutations may be used according to the invention; for example, such mutations include mutations of genes set forth supra or the following mutations, which exist in strains of mice named for the mutation, such as dominant white spotting (W), a mutation of the receptor/kinase for c-kit; patch (Ph), a mutation of the platelet derived growth factor receptor alpha subunit (Stephenson et al., 1991, Proc. Natl. Acad. Sci. U.S.A. 88:6–10); and Steel, a mutation of the ligand for c-kit, mast cell growth factor.

The effect of the knock-out or naturally occurring mutation on melanoma susceptibility can be evaluated by quantitating the susceptibility of an animal containing such a knock-out or naturally occurring mutation to melanoma, or by breeding the animal carrying the knock-out or natural mutation with a melanoma-susceptible animal as described in Section 5.1., supra and determining the incidence of melanoma in the offspring.

For example, and not by way of limitation, a Patch mouse may be mated with a melanoma-susceptible transgenic mouse (preferably having a C57BL/6 strain background, as does Patch; e.g. a C57/BL6-Tyr-SV40E mouse of a line determined to be highly susceptible to melanoma). The proclivity of the offspring (or lines established therefrom) of such a cross to develop melanoma may then be quantitated and compared to melanoma incidence in the parental transgenic lines. A decreased incidence of melanoma in the offspring relative to the melanoma-susceptible parental line indicates that the platelet derived growth factor receptor may affect signal transduction so as to influence melanomagenesis.

In additional embodiments, a knock-out or natural mutation may increase susceptibility to melanoma if it eliminates a gene associated with the melanocyte differentiated phenotype. For example, a knock-out mutation of the non-erythrocyte spectrin gene may impair the formation of dendrites on melanocytes and facilitate closer association of the cells, as occurs in early stages of melanoma. Or, if a tumor suppressor gene, e.g., p53, is inactivated, melanomagenesis may increase.

In still further embodiments of the invention, an effect tantamount to an engineered knock-out mutation may be achieved using an inducible promoter. For example, if a transgene carried by a line of melanoma-susceptible transgenic animals is controlled by an inducible promoter, the incidence of melanoma in these animals in the presence (gene "on") or absence (gene "off") of inducing agent may be compared. As a specific, non-limiting embodiment of the invention, a line of transgenic animals may be produced that carries one transgene that is an oncogene under the control of the tyrosinase promoter and another transgene that is the p53 tumor suppressor gene under the control of the inducible metallothionein promoter.

5.5. CELL LINES

The present invention also provides for cell culture lines derived from transgenic animals prepared as described in Section 5.1. supra. For example, a cell line may be derived from melanoma cells obtained from a tumor in a transgenic animal that was produced according to the invention. Alternatively, cell lines may be prepared from non-tumor melanocytes of the transgenic animal.

The animals of certain transgenic lines may consistently be less pigmented than others, and some areas within an animal of a certain line may be less pigmented than others. It has also been observed that pigment cells from transgenic animals having an oncogene transgene which are relatively lighter in color appear to express higher levels of oncogene product compared to cells from darker animals. These lighter cells may be less differentiated due to increased oncogene expression and may also be more susceptible to transformation. Accordingly, cell lines derived from less pigmented cells may be utilized as highly sensitive assay systems for identification of carcinogens, particularly melanoma inducing agents.

Further, melanocyte cell lines from darker colored transgenic mice may be used to determine gradual genetic changes as the cells become transformed; and to detect changes induced by carcinogens in early phases of premalignancy.

In additional embodiments, cell lines may be prepared by the insertion of a nucleic acid construct comprising a "transgene" described in Section 5.1., and be directly used to generate a transformed cell line. Suitable cells include cells harvested from an animal as well as cells which are members of an immortalized cell line. In preferred embodiments of the invention, the cells are pigment cells. The recombinant nucleic acid constructs may be introduced into the cells by any method known in the art, including, but not limited to, transfection, retroviral infection, microinjection, electroporation, transduction, DEAE-dextran, etc. Cells which express the recombinant construct may be identified by directly or indirectly detecting the "transgene" product. For example, if the "transgene" is an oncogene, and pigment cells have been transfected with a recombinant construct comprising the oncogene under the control of a pigment cell-specific promoter, transfected cells may be isolated by limiting dilution into microtiter wells or may be plated in soft agar. Cells which express the oncogene may be identified using an anti-oncogene product antibody or by detecting rapid proliferation or transformation of the cells. Alternatively, a second recombinant nucleic acid construct comprising a reporter gene under the control of the same promoter which is used to produce selective expression of the "transgene" may be cotransfected into cells together with the constructs of the invention; cells which express the gene of interest may be identified indirectly by the detection of reporter gene expression. Any reporter gene known in the art may be utilized, including, but not limited to, beta-galactosidase, beta-glucuronidase, neo, chloramphenical acetyltransferase, etc.

Pigment cell line cultures produced according to the invention may benefit from the addition of cellular factors, including, but not limited to, melanocyte stimulating hormone. Furthermore, the cell lines of the invention may benefit from coculture with other cells which may produce factors conducive to cell growth.

The cell lines of the invention may be used to identify carcinogens as well as anti-melanoma agents in methods analogous to those which utilize transgenic animal model systems (see infra). In particular embodiments, cell lines exposed to a test agent which is a potential carcinogen may be assayed for transformation. For example, the cell lines of the invention may be exposed to ultraviolet light and evaluated for transformation. A dose-response relationship between test agent concentration and percent transformation may be established for a given agent and then compared to the dose-response relationship of known carcinogens to transformation frequency. Similarly, the growth or differentiation state of transformed pigment cell lines may be used to evaluate potential chemotherapeutic agents for the desirable ability to destroy, inhibit proliferation, or promote differentiation of transformed pigment cells.

If a cell line of the invention is to be used in the study of melanoma induction by agents such as ultraviolet light, it may be desirable for that cell line to consist of susceptible cells that are untransformed and have a relatively low rate of spontaneous transformation. For example, and not by way of limitation, a transgenic cell line used to study the tumorigenicity of ultraviolet B radiation in Section 7., infra, did not progress to spontaneous focus formation at confluence until passage 77; earlier, at passage 57, only a few low pile-ups of cells, termed "abortive foci," appeared and the cells not in contact with the plastic substrate soon died or ceased to divide. Accordingly, cells of this line were used to study ultraviolet B-induced transformation at passages 17, 23, 32 and 43, significantly before abortive foci or transformation was likely to occur.

5.6. USE OF TRANSGENIC ANIMAL SYSTEMS TO STUDY HUMAN CUTANEOUS MELANOMA

The transgenic animal systems described supra may be used to study human cutaneous melanoma in a number of ways.

For example, such models may be used to study the genetic basis for melanoma formation and progression by quantitating and comparing the susceptibility of various transgenic animals of the invention to melanoma. For example, if transgenic animals carrying and overexpressing a transgene encoding a particular growth factor or growth factor receptor are exceptionally susceptible to melanoma, a role for that growth factor or growth factor receptor in the disease would be implied.

Further, the susceptibility of offspring of crosses involving at least one parent that is a transgenic animal of the invention to melanoma may be used to evaluate the roles of various genes in melanoma formation and progression. Thus, the incidence of melanoma may be measured in lines developed from offspring of a cross between one parent, "X" that is a transgenic animal carrying an , oncogene transgene of a line that is melanoma susceptible and a second parent, , "Y" that is a transgenic animal carrying a transgene encoding a growth factor receptor of a line that is moderately susceptible to melanoma. If the offspring exhibit an incidence of melanoma greater than either the lines of X or Y, the growth factor receptor is implicated in the origin or progression of melanoma.

Melanomas and earlier lesions arising in the transgenic animals of the invention (or corresponding cell lines) may also be analyzed for the production of specific growth factors in order to determine whether, in transformation and progression toward malignancy, there has been a shift from paracrine dependence for the factor on other cells (e.g. keratinocytes, fibroblasts) to autocrine production, resulting in increased growth autonomy by the tumor cells.

Such analyses may determine the level of expression of a particular growth factor in a lesion (benign, premalignant, or malignant) from a transgenic animal of the invention. The level of expression may be determined by either measuring levels of the factor itself using, for example, biochemical or immunological (e.g. ELISA, radioimmunoassay, etc.) assays, or biological assays which measure the amount of growth factor activity using cultures of cells known in the art to be sensitive to the particular growth factor. Alternatively, levels of mRNA encoding the growth factor may be measured, for example, by Northern blot analysis.

For example, and not by way of limitation,levels of expression of the following growth factors may be measured: basic fibroblast growth factor, acidic fibroblast growth factor, transforming growth factor alpha, transforming growth factor beta, keratinocyte growth factor, platelet derived growth factor alpha or beta, hepatocyte growth factor/scatter factor, mast cell growth factor, interferon gamma, interleukin-1, interleukin-6, interleukin-7, tumor necrosis factor alpha, tumor necrosis factor beta, melanoma growth stimulating activity or epidermal growth factor.

It further may be desirable to ascertain the level of expression of a growth factor receptor by cells of the lesion, including, but not limited to, receptors for the growth factors listed supra. Receptor expression may be studied by measuring levels of receptor protein or mRNA, or by quantitating binding to detectably labeled ligand (i.e. growth factor), for example using in situ binding or cell-sorting techniques.

Further, the response of cells derived from transgenic animal lesions to growth factors may be evaluated by studying the growth characteristics of such cells in various types of medium or culture conditions, and to compare these characteristics to the growth characteristics of control cells (e.g. untransformed melanocytes from he same transgenic animal or melanocytes from a non-transgenic animal). For example, cells from a lesion may be cultured in the presence or absence of growth factor "X". The growth rate of these cells may then be determined (e.g. by tritiated thymidine incorporation or cell number) and compared to the growth rate of normal melanocytes from both the same transgenic animal and a non-transgenic animal,under comparable conditions. If the non-transgenic animal cells grow at a significantly higher rate in the presence of growth factor compared to in the absence of growth factor, but cells from the lesion grow comparably well in the presence or absence of growth factor, then the cells from the lesion may have developed autocrine production of the growth factor. The response of normal melanocytes from the transgenic animal to growth factor may indicate whether transition to autocrine production of growth factor occurred early or late in the development of the lesion. Similar experiments, which evaluate the effects of coculturing cells obtained from the lesion with other cells (e.g. keratinocytes or fibroblasts) or cell supernatants may also be used to detect autocrine production of growth factors.

In additional embodiments, melanomas and earlier lesions arising in the transgenic animals of the invention (or corresponding cell lines) may be analyzed for changes in specific gene expression during transformation and progression toward malignancy, including increases as well as decreases in gene expression. Such analyses may be performed using techniques such as subtractive hybridization and/or differential screening of cDNA libraries prepared from different stages of melanoma development.

As a non-limiting example of the former, CDNA may be prepared from cells derived from a lesion and then hybridized to an excess of polyA$^+$ mRNA from normal melanocytes or an untransformed melanocyte cell line; such MRNA may, desirably, be conjugated to biotin. After a period of time sufficient to allow hybridization to occur, the hybridization mixture may then be passed through a streptavidin column; cDNA corresponding to normal melanocyte mRNA, as well as excess mRNA, should be retained on the column, while the flow-through may be expected to contain lesion-specific cDNA, which may then be cloned and propagated.

As a non-limiting example of the latter, cDNA libraries may be prepared from lesions representing various stages of melanoma, and cDNAs unique to each stage identified. As a specific, illustrative example cDNA libraries may be prepared from normal melanocytes (library "N"), pre-malignant melanocytes (library "P"), early melanoma (library "M") and advanced melanoma (library "A"). cDNA from an early melanoma may be subtractively hybridized with untransformed melanocyte mRNA as set forth supra, and the unhybridized portion labeled to form a probe which is used to screen libraries N, P, M, and A. Failure to identify clones in N and P would be consistent with the probe being truly melanoma-specific. The probe may desirably identify melanoma-specific clones in libraries M and A. A similar procedure could then be performed, using advanced melanoma cDNA subtractively hybridized with early melanoma RNA, to identify clones of cDNA representing genes expressed specifically in advanced melanoma.

In further embodiments, the transgenic animals of the invention may be used to identify agents that may promote melanoma formation. Such agents include chemical compounds as well as light (e.g. ultraviolet B light, ultraviolet A light). The ability of an agent to increase incidence of melanoma in a transgenic animal of the invention relative to other, non-exposed animals of the same transgenic line indicates that the agent may promote human melanoma formation.

Similarly, the transgenic animals of the invention may be used to identify agents that inhibit melanoma formation and that may be used in prophylactic treatment regimens or in the therapy of existing melanoma. For example, a compound being tested for sunscreen activity may be topically applied to animals from a melanoma-susceptible transgenic line, these animals may be irradiated with ultraviolet light, and the incidence of melanoma can be determined and compared to the incidence of melanoma in irradiated animals of the same line that had not been treated with the putative sunscreen. Or, as another example, a transgenic animal of the invention which has developed melanoma may be treated with a compound being tested for anti-melanoma activity (e.g. an antagonist of growth factor activity such as a compound that blocks binding of a specific growth factor to its receptor); a halt or slowing of progression of the disease in the animal relative to an untreated, equivalent animal (i.e. another transgenic animal of the same line with comparable disease) would correlate positively with anti-melanoma activity of the test compound.

Further, discerning the roles of various genes in the origin and progression of human cutaneous melanoma may be expected to suggest diagnostic and therapeutic methods to be applied toward the prevention, diagnosis, grading, and treatment of human disease.

6. EXAMPLE: METASTATIC CUTANEOUS MELANOMA INDUCED IN TRANSGENIC MICE BY SKIN GRAFTING

6.1. MATERIALS AND METHODS
6.1.1. TRANSGENIC MICE

For the construction and preparation of Tyr-SV40E, the SV40 early region, including the coding sequences of the transforming large tumor (T) and small tumor (t) antigens (Fiers et al., 1978, Nature 273:113–120) and extending from the AvrII (nucleotide 5187) to the BamHI (nucleotide 2533) restriction site, was excised from p6-1Δ. An AvrII/BglII/SmaI adaptor was ligated to the AvrII site, and the fragment was cleaved with BglII. Two and one-half kilobases of 5' flanking sequence of the mouse tyrosinase gene was derived from ΔgTYR101 (Ruppert et al., 1988, EMBO J. 7:2715–2722) and was used as a promoter. This fragment was bounded by an EcoRI site and a Sau3A site 65 base pairs downstream of the major transcription start site (Ruppert et al., 1988, EMBO J. 7:2715–2722; Yamamoto et al., 1989, Jpn. J. Genet. 64:121–135) and 15 base pairs upstream of the initiation codon. The tyrosinase promoter was ligated, in the vector PBS, to the BglII/BamHI fragment of SV40 early region to generate Tyr-SV40E (FIG. 1). The EcoRI/BamHI fragment containing the mouse tyrosinase promoter and the coding regions of SV40 early genes was separated from vector DNA by gel electrophoresis. It was purified for microinjection by using Geneclean (Bio 101, La Jolla, Calif.) and diluted to a final concentration of 1.5 μg/ml in DNA injection buffer (5 mM Tris/0.1M EDTA).

Transgenic mice were produced essentially as described in Wagner et al., 1981, Proc. Natl. Acad. Sci. U.S.A. 78.:5016–5020. Briefly, black inbred C57BL/6 (Icr subline) prepuberal females were superovulated and mated to C57BL/6 males. The fertilized eggs were microinjected with approximately one picoliter of DNA, corresponding to 300 copies of the transgene. Embryos were transferred, together with uninjected carrier embryos of the albino random-bred ICR strain, to oviducts of ICR pseudopregnant females.

The resulting offspring were then tested, by Southern blot analysis, to identify true transgenic mice carrying the Tyr-SV40E transgene. From among the transgenic mice identified, those carrying a single copy or tandem copies of the transgene were then used to establish individual lines of mice (transgenic mice having multiple transgene integration sites were excluded from this study).

Certain lines of transgenic animals, typically those with higher copy numbers of the transgene, exhibited high susceptibility to melanoma development, characterized by early development of ocular melanoma, aggressive tumor growth often leading to death prior to cutaneous melanoma development, and, frequently, metastatic disease. Other lines manifested relatively low susceptibility to melanoma formation.

6.1.2. SKIN GRAFTING PROCEDURE

Skin from a high susceptibility transgenic mouse donor was grafted onto a juvenile low susceptibility transgenic mouse host as follows.

Full-thickness skin was excised from a donor transgenic mouse of a line exhibiting a high susceptibility to melanoma preferably before advanced eye tumor was present, and, using sterile technique, was placed on a graft bed of slightly larger size cleared of skin on the trunk of a transgenic mouse host from a line exhibiting low susceptibility to melanoma. The graft was then sprinkled with a small amount of antibiotic-containing powder, such as Nitrofurazone, overlaid with petroleum jelly impregnated gauze, and then wrapped in place with a plaster bandage.

6.2. RESULTS AND DISCUSSION

Over time, it was observed that melanomas arose at an accelerated rate at or near the borders of grafted skin.

Figure 2A:
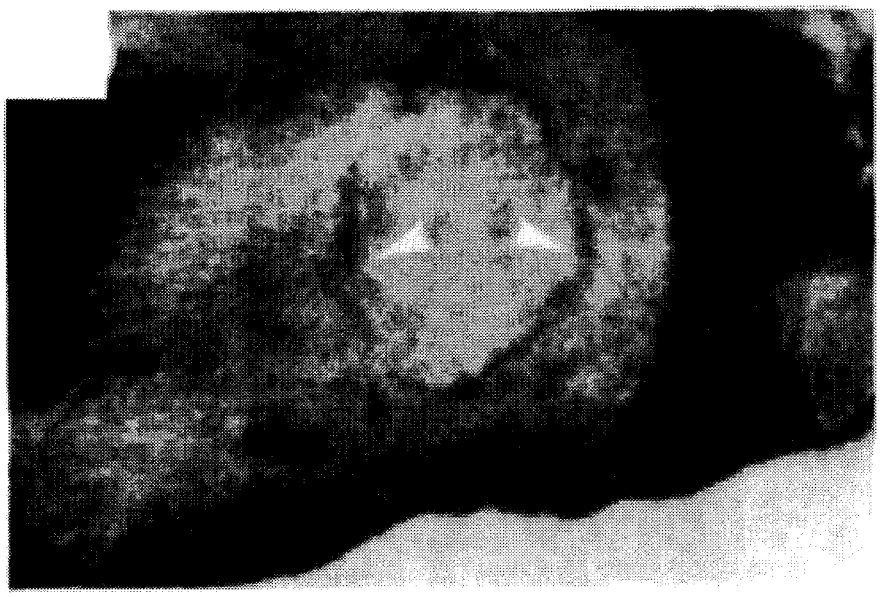

As shown in FIG. 2(a), shortly after the wound bordering the graft had closed, a large number of heavily pigmented macules developed at the edges of the graft, creating the appearance of a dark outline of the graft. It was also noted (FIG. 2(b)) that the skin surrounding the graft was subject to tearing and appeared more fragile than similarly situated tissue in skin grafts involving non-transgenic animals.

Figure 2B:
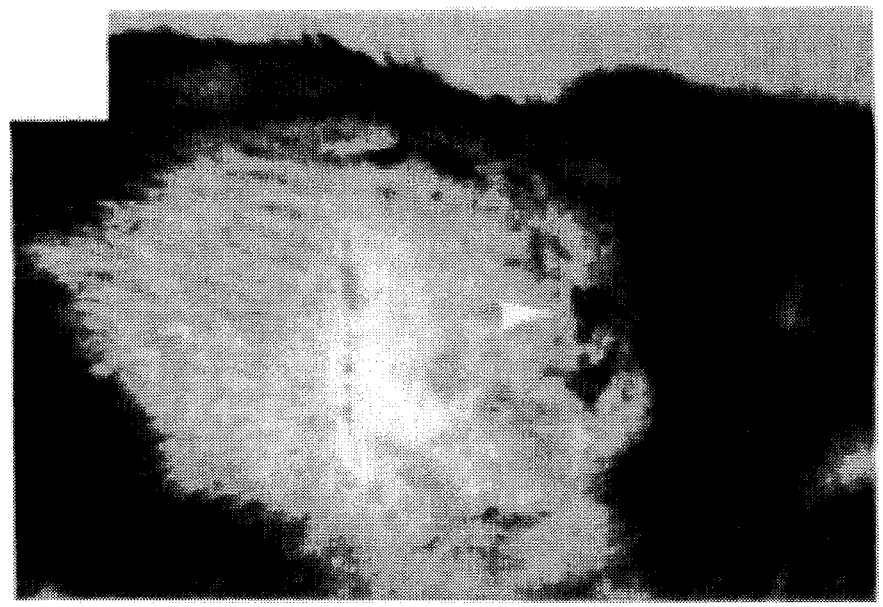
Figure 2C:
Figure 2D:
Figure 2E:
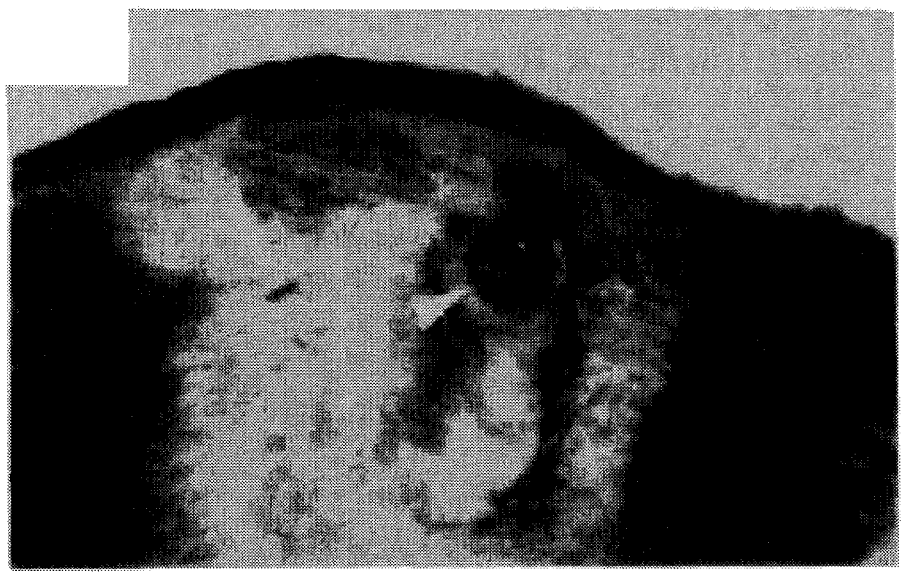
Figure 2F:

Although pigmented macules or nevi occasionally appeared in the interior region of the graft (FIG. 2(c), small arrow), those early lesions appeared much more frequently near the graft borders (FIG. 2(c), large arrow). They became melanomas which rapidly broke through the skin surface and invaded contiguous tissues (FIGS. 2(d), 2(e) and 2(f)). Such melanomas were found to metastasize to organs such as the lymph nodes and lung and lymph nodes. (FIGS. 3(f), 3(g), and 3(h)).

Figure 3A:
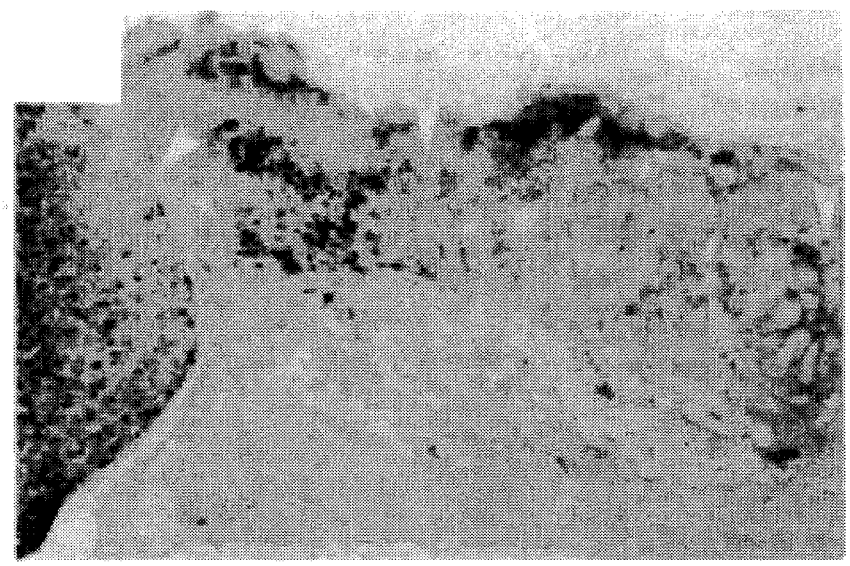
Figure 3B:
Figure 3C:
Figure 3D:
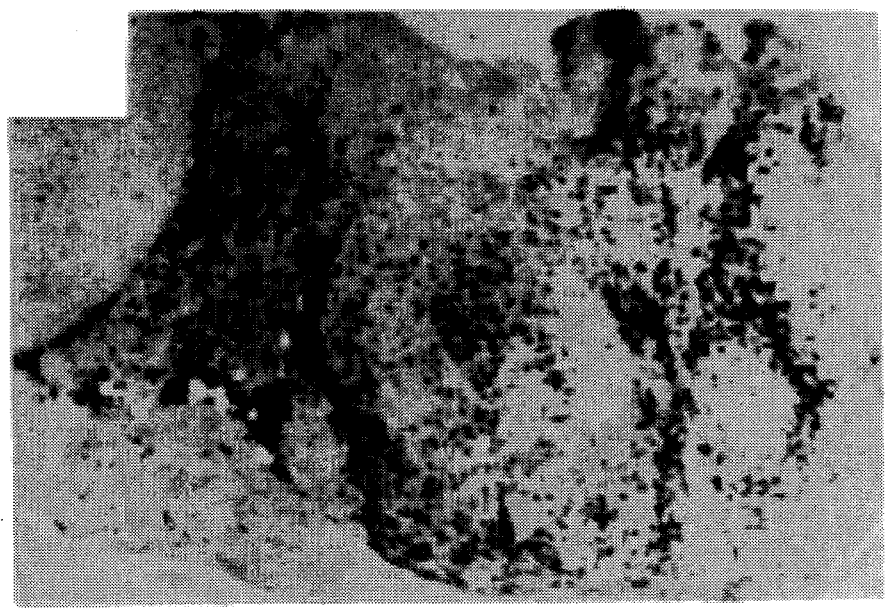

Histologically, these melanomas were found sometimes to be lobulated tumors (FIG. 3(d)). The earliest lesions were characteristic clusters of very darkly pigmented dendritic cells (FIGS. 3(a) and 3(b)) followed by gradual loss of dendrites and pigment and occurrence of cohesion of the cells (FIGS. 3(a)–3(c)). The later, hypopigmented stages may represent more malignant cells. The lobulated nature of some of the tumors may result from clonal variation as the tumor develops or be indicative of a polyclonal origin.

Figure 3E:
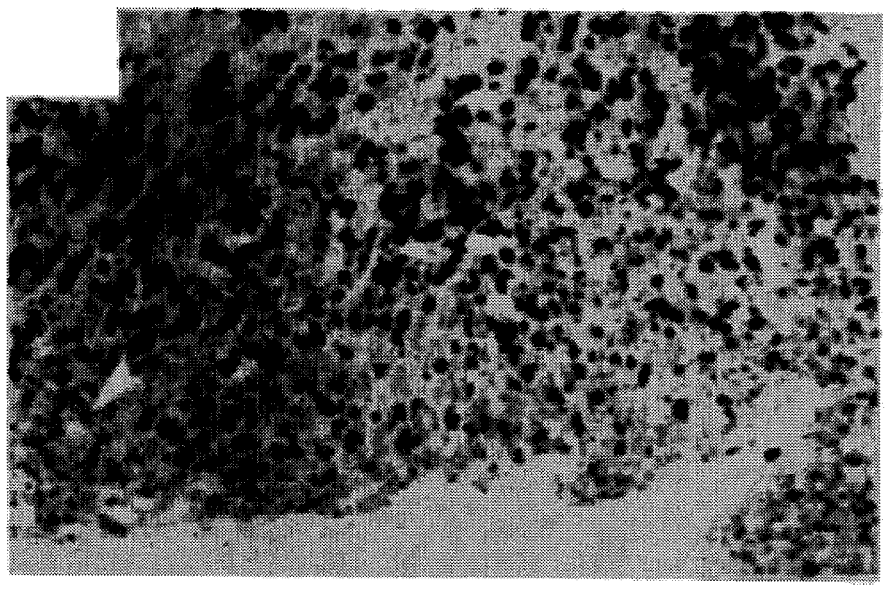
Figure 3F:
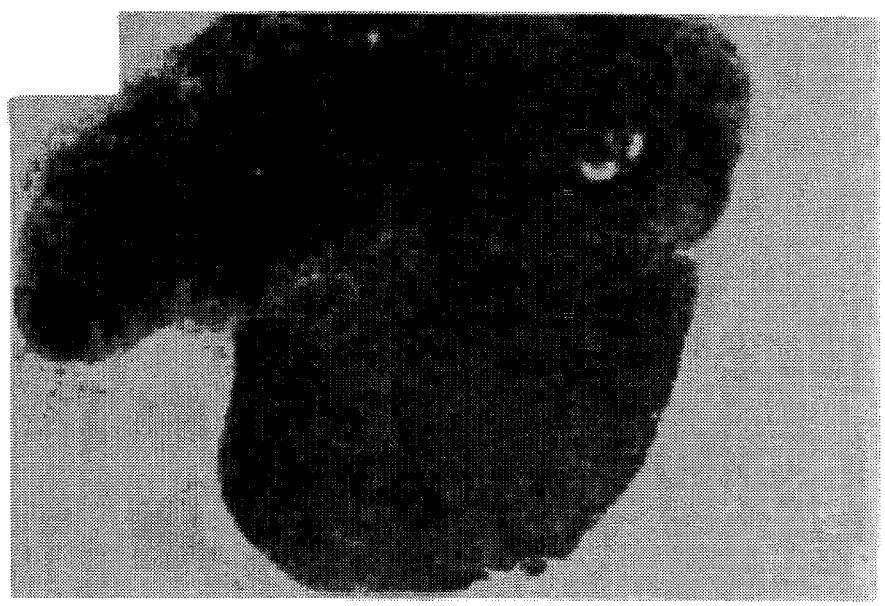
Figure 3G:
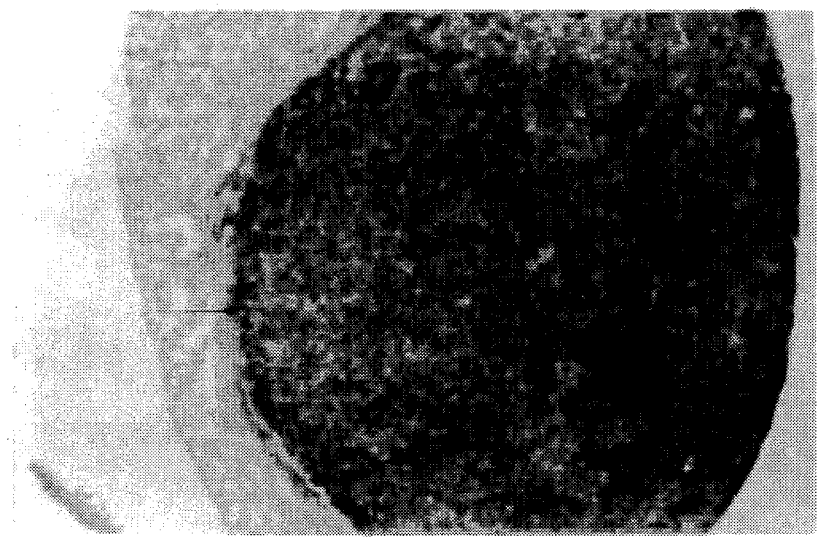
Figure 3H:
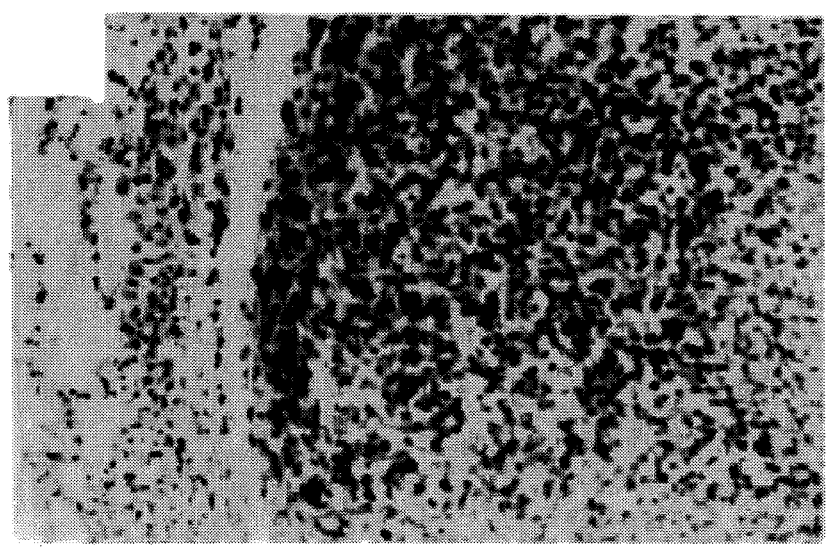

As evidence of the aggressiveness of these melanomas, local invasion was rapid, (FIG. 2(b), (d–f)) and expansion occurred in tumor width as well as depth. The ability of these melanomas to penetrate deep into tissues is illustrated in FIG. 3(e), which shows tumor involvement of underlying muscle and subcutaneous tissue, and parallels the behavior of human melanoma (in which the depth of penetration by tumor correlates with aggressiveness of the disease and its prognosis).

Southern blot analysis confirmed that the melanomas arising in the graft as well as their metastases in lung originated from the graft itself rather than from the host, i.e. from skin obtained from a transgenic mouse highly susceptible to melanoma.

7. EXAMPLE:GENETIC PREDISPOSITION OF TRANSGENIC MOUSE MELANOCYTES TO MELANOMA RESULTS IN MALIGNANT MELANOMA AFTER EXPOSURE TO A LOW ULTRAVIOLET B INTENSITY THAT IS NONTUMORIGENIC FOR NORMAL MELANOCYTES

7.1. MATERIALS AND METHODS
7.1.1. MELANOCYTE LINES

Skin melanocyte lines were derived by procedures set forth in Eisinger and Marko, 1982, Proc. Natl. Acad. Sci. U.S.A. 79:2018–2022; and Tamura et al., 1987, In Vitro Cell. Dev. Biol. 23:519–522, from one-week-old mice: some lines were from wild-type C57BL/6 inbred-strain mice and some were from Tyr-SV40E hemizygous transgenic mice of line 9 (Bradl et al., 1991, Proc. Natl. Acad. Sci. U.S.A. 88:164–168) on the same strain background. The cells for each line were explanted from skin after removal of the epidermis and cultured in the standard medium containing the phorbol ester phorbol 12-myristate 13-acetate (PMA) acting as a growth factor, dibutyryl-cAMP, human placental extract, and 20% (vol/vol) fetal calf serum (FCS) in Ham's F10 solution with added glutamine, penicillin, and streptomycin.

7.1.2. IRRADIATION WITH UV LIGHT

A UVM-57 mid-range lamp (UVP, San Gabriel, Calif.) with a continuous spectrum from 275 to 380 nm and a peak emission at 310-nm wavelength was used. The lamp was equipped with a filter whose transmission characteristics restrict most of the energy passing through to UVB. The energy actually reaching the cells was measured with a digital radiometer and sensor (UVX-31; UVP) with a peak sensitivity calibrated at 310 nm. From calculations based on curves (obtained from UVP) recording the spectral energy distribution of the lamp, the transmission profile of the filter, and the spectral response of the sensor, 70.0% of the total irradiance to which the cells were exposed was in the UVB range (280–320 nm); 29.7% was in the lower end (320–380 nm) of the ultraviolet A range (320–400 nm); and a very minor component (0.3%) was in the upper end (275–280 nm) of the ultraviolet C range (100–280 nm).

The lamp was positioned in a closed black chamber so that the distance from the light source to the cells could be adjusted. The distance and time of exposure necessary to obtain the desired intensity of UVB radiation were calibrated for each set of experiments. Before choosing the experimental levels of UVB radiation, the lethal doses that killed various percentages of the cells ($LD_{20}$, $LD_{40}$, etc.), counted 24 hr after irradiation, were separately determined for the transgenic and the wild-type cells, at culture passages of each at which the doubling times and melanin content had become stabilized. An example of the conditions in a subsequent experimental set is as follows: at a distance of 45 cm, an exposure of 10 sec delivered a total irradiance of 1 $mJ/cm^2$ of which 0.7 $mJ/cm^2$ was UVB; an exposure of 25 sec delivered a total of 2.5 $mJ/cm^2$ of which 1.75 $mJ/cm^2$ was UVB.

The cells were seeded in Petri dishes of 6-cm or 10-cm diameter at 150,000 or 300,000 cells, respectively, in the standard medium. Before irradiation, the medium was aspirated and replaced with phosphate-buffered saline (PBS) to avoid formation of toxic photodegradation products from some of the components in the standard medium. After irradiation, the PBS was replaced with fresh standard medium. Similar changes were made concurrently in unirradiated cultures of transgenic and wild-type cells. Aliquots of the cultures prior to irradiation were tested for anchorage independence by their ability to form foci at confluence and were found to be negative. To test for formation of foci after exposure to UVB radiation, the cultures in several dishes from the same irradiation conditions were dissociated and pooled 24 hr after UVB treatment and transferred to a flask for attachment to the plastic. In this way, individual foci that might later form at confluence would be more likely to reflect separate genetic changes than in the reverse procedure prolonged growth in the original dishes followed by pooling. The latter was used in a preliminary experiment but was supplanted as it was expected to scatter and reseed identical mitotic descendants of far fewer cells that were genetically changed. (A comparison of the two procedures did indeed verify that substantially more foci appeared if the cells were first propagated in place for 9 days and then pooled.) One dish was reserved for a cell count 24 hr after UVB.

Some flasks of irradiated cells were kept in the standard medium to test their subsequent ability to grow. In most cases, cells were shifted to a selection medium, starting 24 hr after irradiation. Inasmuch as transformed or tumorigenic cells, but not normal cells, can grow with a greatly reduced exogenous source of growth factors, the selection media were intended to isolate cells progressing toward tumorigenesis. These might be expected to form foci when they became anchorage independent. The most stringent selection medium, used in some cases, lacked PMA, dibutyryl-cAMP, and human placental extract and had 5% instead of 20% FCS; hereafter this is referred to as Ham's/5% FCS. In other cases, a less stringent selection medium was used, based on ability of the cells to grow without PMA, if transformed; this medium, designated "AP" in Table 1, lacked only PMA as compared with the standard medium and had 2% serum.

7.1.3. ASSAYS FOR MELANIN CONTENT

The irradiated dish used for a cell count 24 hr after UVB treatment was also used to determine melanin content. The cells were centrifuged, washed with PBS, and recentrifuged. One million cells in 100 μl of 1M NaOH were vortexed for 15 min. The absorption baseline was established with 1M NaOH, and the melanin content was measured at 475 nm with various numbers of cells. A homopolymer of dopaquinone (Sigma) served as a melanin standard.

7.1.4. TESTS FOR TUMORIGENICITY

Exponentially growing cells from the cultures were assayed for their ability to form tumors in vivo by injecting ≈2–5×10$^6$ cells subcutaneously into 6- to 8-week-old immune-deficient athymic nude mice of the same strain (nu/nu-C57BL/6). Tumors were fixed in formalin or Omnifix (Zymed) for histology. The injected cells came from one of three sources. If foci had formed in a culture, a closely spaced group of foci was isolated with a cloning ring and the cells were dissociated and subcultured for further growth, to obtain sufficient cells for inoculation. Equivalent areas of cells were ring-isolated and grown, either from a focus-free part of the same flask or from a flask entirely lacking foci.

7.2. RESULTS

7.2.1. CYTOTOXICITY OF UVB

From counts of cells surviving 24 hr after a single exposure, in comparison with unirradiated cells, the wild-type cells were less sensitive to UVB-induced damage than were transgenic cells, at the UVB intensities of 0.7–17.5 mJ/cm$^2$ that were tested in both (FIG. 4) The intensity that killed 20%, 40% and 60% Of transgenic cells ($LD_{20}$, $LD_{40}$, and $LD_{60}$) was 0.7, 1.75, and 3.5 mJ/cm$^2$ of UVB irradiation (in approximately 1, 2.5, and 5 mJ/cm$^2$ of total irradiation). Therefore, 0.7 and 1.75 mJ/cm$^2$ of UVB irradiation were chosen for further experiments.

7.2.2. INDUCTION OF MELANIZATION BY UVB

The transgenic cells were hypomelanotic when the cell line was stabilized; this is consistent with the grey coat color of the animals (Bradl et al., 1991, Proc. Natl. Acad. Sci. U.S.A. 88:164–168; Klein-Szanto et al., 1991, Proc. Natl. Acad. Sci. U.S.A. 88:169–173), which were genetically black (B/B). Before irradiation, the approximate melanin content was 70 pg per transgenic cell, whereas it was 200 pg per cell in the wild-type line. In the absence of UV treatment, these values remained constant. After exposure to 3.5 mJ/cm$^2$ of UVB, the amount of melanin in the transgenic cells rose sharply to 105 pg per cell (FIG. 5). Melanin did not increase in wild-type cells at these low intensities, but rose thereafter, up to 300 pg per cell at 35 mJ/cm$^2$. (Measurements were not made of transgenic cells at higher intensities because of their limited viability.) Therefore, the maximum induction was the same in the two genotypes: 1.5-fold at 3.5 mJ/cm$^2$ of UVB for the transgenic cells and 1.5-fold at 35 mJ/cm$^2$ for the wild-type cells.

7.2.3. ANCHORAGE INDEPENDENCE AFTER UVB

The transgenic cells reached confluence and formed foci sooner after exposure to the higher UVB intensity. After 1.75 mJ/cm$^2$ of UVB, foci appeared in the more stringent selection medium (Ham's/5% FCS) after 11 weeks and in the less stringent medium (AP) after only 2 weeks. Following exposure (at the same culture passage) to 0.7 mJ/cm$^2$ of UVB, foci appeared after 25 weeks in the Ham's/5% FCS medium; a parallel culture in the AP medium was lost to contamination.

Foci that formed in the transgenic cultures after the higher UVB intensity were also much more numerous and were more widely and evenly distributed than after the lower intensity; the foci were generally larger and thicker (FIG. 6) as well. The results are consistent with a relatively greater number of independent mutational events occurring in response to the higher UVB dose. Foci did not appear in untreated or in UVB-treated wild-type cells, even after 1.75 mJ/cm$^2$ exposure (Table 1).

The transgenic cells of the particular explant line used in this study were at culture passages 17, 23, 32, and 43. Unirradiated cells of this specific line did not progress to spontaneous focus formation at confluence until passage 77; at passage 57, a few low pileups of cells, termed "abortive foci," appeared, but the cells not in contact with the plastic soon died or ceased to divide. In an exceptional case, a culture tested at passage 32 formed a single closely spaced group of small foci in the Ham's/5% FCS medium; the rarity of this group implies that a single spontaneous genetic change had arisen in one cell and was transmitted in a small mitotic clone. The possibility of such rare events at a relatively early culture passage was confirmed in an independent repetition of the test.

7.2.4. TUMORIGENICITY AFTER UVB

Each group of foci, or comparable area of cells without foci, that was isolated with a cloning ring was dissociated and initially placed in a small volume of medium, either in a well of a 24-well plate or in a small Petri dish. As the number of cells increased, the cells were transferred to progressively larger dishes or flasks. When there were very large numbers of foci (after 1.75 mJ/cm$^2$ of UVB), they were removed by light trypsinization of the entire culture, yielding sufficient cells for growth in a larger volume of medium, for fewer subsequent passages. The numbers of postirradiation passages before cell inoculations are shown in Table 1.

As is evident from Table 1, focus formation—albeit a classic phenotype of transformation in cultured cells—is not tantamount to tumorigenicity in vivo. Transgenic cells from foci that arose after 0.7 mJ/cm$^2$ of UVB failed to yield tumors in graft hosts kept under observation for 6 months. In contrast, cells from foci appearing after 1.75 mJ/cm$^2$ of UVB were tumorigenic, irrespective of the type of selection medium in which they had been grown. The tumors were relatively undifferentiated and amelanotic, with a mixture of spindle and epithelioid cells, sometimes invading neighboring tissue (FIG. 7).

TABLE 1

Tumorigenic effect of UVB irradiation of cultured transgenic melanocytes containing simian virus 40 oncongenic sequences

| Melanocyte line | Passage no. at UVB | UVB intensity mJ/cm$^2$ | Selection medium | Foci formation | Passages grown after UVB | Source of grafted cells | Cell pigmentation | Hosts with tumors/ total hosts |
|---|---|---|---|---|---|---|---|---|
| Transgenic | 32 | 0.7 | Ham's/5% FCS | + | 27 | Foci | Light | 0/3 |
|  |  |  |  |  |  | Nonfoci | Light | 0/3 |
|  | 32 | 0.7 | Ham's/5% FCS | + | 31 | Foci | Light | 0/3 |
|  | 32 | 1.75 | Ham's/5% FCS | + | 10 | Foci | Light | 7/7 |
|  | 32 | 1.75 | AP | + | 21 | Foci | Light | 4/4 |
| Wild type | 32 | — | Ham's/5% FCS | − | 7 | Nonfoci | Dark | 0/3 |
|  | 32 | 1.75 | Ham's/5% FCS | − | 10 | Nonfoci | Dark | 0/3 |
|  | 18 | — | Standard | − | — | Nonfoci | Dark | 0/6 |

7.3 DISCUSSION

Melanocytes of an in vitro cell line derived from a Tyr-SV40E transgenic mouse were irradiated with very low intensities of ultraviolet B (UVB) (280- to 320-nm wavelength) light at culture passages when the cells had not achieved anchorage independence. After a single exposure to 0.7 mJ/cm$^2$ of UVB radiation, the cells became anchorage independent and formed foci at confluence; however, cells propagated from the foci were not tumorigenic. After one exposure to 1.75 mJ/cm$^2$, more numerous and larger foci resulted, and the cells grown from them yielded malignant melanomas in graft hosts. Wild-type melanocytes were not transformed at these UVB doses. At least two genetic changes contributing to malignant conversion—in addition to the initiating effect of the transgene—are likely to have occurred, one change leading to anchorage independence and another to further progress toward malignancy. Cells at these stages provide an opportunity to isolate the relevant genes and identify any molecular defects attributable to UVB. Tumorigenesis after a very low UVB dose in cells where an initiating stimulus is already present suggests that some other stimulus, such as a gene product or a carcinogen, may lead to melanoma in conjunction with exposure to relatively little UVB.

Various publications are cited herein that are hereby incorporated by reference in their entirety.

What is claimed is:

1. A method for producing a transgenic mouse that develops cutaneous melanoma, comprising grafting a portion of skin from a first donor transgenic mouse onto a second histocompatible recipient transgenic mouse, in which:

(a) both the donor and recipient transgenic mice are more susceptible than wild-type mice to developing cutaneous melanoma, and (b) the donor mouse is from a line characterized by early development of ocular melanoma and aggressive ocular tumor growth, and (c) the phenotype of each transgenic mouse is conferred by an SV40E oncogene, the expression of which is controlled by a pigment cell-specific tyrosinase gene promoter, so that nevi and cutaneous melanomas develop within the graft.

2. The transgenic mouse produced according to the method of claim 1.

* * * * *